US006156883A

United States Patent [19]
Estes et al.

[11] Patent Number: 6,156,883
[45] Date of Patent: Dec. 5, 2000

[54] POLYCLONAL AND MONOCLONAL ANTIBODIES TO NORWALK VIRUS AND METHODS FOR MAKING THEM

[75] Inventors: Mary K. Estes, Friendswood; Xi Jiang; David Y. Graham, both of Houston, all of Tex.

[73] Assignee: Baylor College of Medicine, Houston, Tex.

[21] Appl. No.: 08/184,885

[22] Filed: Feb. 4, 1993

Related U.S. Application Data

[63] Continuation of application No. 07/573,509, Aug. 27, 1990, abandoned, which is a continuation-in-part of application No. 07/515,993, Apr. 27, 1990, abandoned, which is a continuation-in-part of application No. 07/433,492, Nov. 8, 1989, abandoned.

[51] Int. Cl.$^7$ .......................... C07K 16/00; C12P 21/04; G01N 33/53
[52] U.S. Cl. .................................. 530/389.4; 530/388.3; 435/70.21; 436/547
[58] Field of Search ............................. 530/389.4, 388.3; 435/240.27, 70.21; 436/547

[56] References Cited

U.S. PATENT DOCUMENTS 4,358,535  11/1982  Falkow et al. .
4,751,080   6/1988  Wyatt et al. .
4,814,268   3/1989  Kreider et al. .

OTHER PUBLICATIONS

Greenberg et al, J. Virol. 37:994–999 Mar. 1981.
Greenberg et al, J. Med Virol 2:97–108, 1978.
Treanor et al, Proc. Natl. Acad. Sci., USA, 85: 3613–3617 May 1988.
Walter, J. Immunol. Meth. 88: 149–161, 1986.
Dresser, Ch 8 of "Handbook of Experimental Immunochemistry" Weir et al, Blackwell Publ v. 1:8.1–8.21 1986.
Norrott, J. Med. Virology 44:280–286, 1994.
Ploegh, PNAS 77:6081–6085, 1980.
T. Tanaka et al.; *High Yield Production of Monoclonal Antibodies to Recombinant Norwalk Virus–Like Particles by Oral Immunization*; Presented at CDC meeting.
Bruce Alberts et al.: *Molecular Biology of The Cell, Second Addition*; Chapter 5; Basic Genetic Mechanisms, 258–266 (1989).
Chitra Mandal et al.; *Production of Highly Specific Polyclonal and Monoclonal Antibodies Using Estradiol–3–O–Carboxymethyl Ether as Hapten*; Steroids 52/5&6, 551–60, Nov. & Dec. 1988.
Ed Harlow et al.; *Antibodies: A Laboratory Manual*; 115, 141, 156–57, 242 (1988).
Bruce Alberts et al.; *Molecular Biology of The Cell, Third Edition*; The Functional Properties of Antibodies, pp. 1211–1227 (1994).
Eli Benjamini et al.; *Immunology: A Short Course, Second Edition*; pp. 174–175 (1991).
Evan M. Roitt et al.; *Immunology*; (1989).
Charles A. Janeway et al.; *Immuno Biology: The Immune System in Health and Disease, Fourth Edition*; pp. 99–100.
Xi Jiang et al.; *Sequence and Genomic Organization of Norwalk Virus*; Virology 195, 51–61 (1993).
Xi Jiang et al.; *Norwalk Virus Genome Cloning and Characterization*; Science, 250:1580–83.
Wang et al.; *Sequence Diversity of Small, Round–Structured Viruses in the Norwalk Virus Group*; Journal of Virology pp. 5982–5990 (1994).
Xi Jiang et al.; *Detection of Norwalk Virus in Stool by Polymerase Chain Reaction*; Journal of Clinical Microbiology pp. 2529–2534 (1992).
Appleton, H. "Small Round Viruses: Classification and Role in Food–Borne Infetions" in Novel Diarrhoea Viruses. (1987) pp. 108–125.
Caul, E.O., et al., J.Medical Virology 9:257–265 (1982).
Cubitt, W.D., et al., J. Infect.Diseases. 156(5):806–814 (1987).
Dingle, J.H., et al., Am. J. Hyg., 58:16–30 (1953).
Dolin, R., et al., Proc. Soc. Exp. Med. & Biol., 140:578–583 (1972).
Dolin, R., et al., J. Infect. Dis., 123:307–312 (1971).
Dupont, H.L., New England J. Med., 314(11):707–708 (1986).

(List continued on next page.)

*Primary Examiner*—Jeffrey Stucker
*Assistant Examiner*—Brett Nelson
*Attorney, Agent, or Firm*—Fulbright & Jaworski L.L.P.

[57] ABSTRACT

Double-stranded cDNA was synthesized from nucleic acid extracted from Norwalk virus purified from stool specimens of volunteers. One clone was isolated from a cDNA library constructed in a pUC-13 vector after amplification of the cDNA. The specificity of this cDNA (pUCNV-953) was shown by hybridization assays. The cDNA reacted with post- (but not pre-) infection stool samples from Norwalk volunteers and with highly purified Norwalk virus, but not with other common enteric viruses such as hepatitis A virus and rotavirus. Finally, the probe detected virus in the same fractions of CsCl gradients in which viral antigen was detected using a specific Norwalk virus radioimmunoassay, and particles were detected by immune electron microscopy. Single-stranded RNA probes derived from the DNA clone after subcloning into an in vitro transcription vector were also used to show that the Norwalk virus contains a ssRNA genome of about 8 kb in size. The original clone was also used to detect additional cDNAs which represent at least 7 kb of nucleic acid of the Norwalk genome. The availability of a Norwalk-specific cDNA and the first partial genome sequence information allow rapid cloning of the entire genome and of establishment of sensitive diagnostic assays. Such assays can be based on detection of Norwalk virus nucleic acid or Norwalk viral antigen using polyclonal or monoclonal antibodies to proteins expressed from the cDNA or to synthetic peptides made based on the knowledge of the genome sequence. Vaccines made by recombinant DNA technology are now feasible.

14 Claims, 10 Drawing Sheets

OTHER PUBLICATIONS

Enzymology, vol. 70, 1980, pp. 104–142.
Geysen, et al., PNAS 8:3998–4002 (1984).
Gill, O.N., et al., Br. Med. J., 287:1532–1534 (1983).
Greenberg, H.B., et al., J. Med. Virol. 2(2):97–108 (1978).
Greenberg, H.B., et al., J. Virol. 37(3):994–999 (1981).
Gunn, R.A., et al., Am. J. Epidemiol., 115:348–351 (1982).
Hayaski, Y., et al., J. Clin. Microbiol., 27:1728–1733 (1989).
Jiang Xi, et al., J. Clin. Microbiol., 27:874–879 (1989).
Jiang Xi, et al., App. Environ. Microbiol., 53:2487–2495 (1987).
Jiang Xi, et al., App. Environ. Microbiol., 52:711–717 (1986).
Kapikian, et al., "Norwalk Group of Viruses" in Field's Virology, (2nd ed. 1990) pp. 671–693.
Kapikian, A.Z., et al., J. Virol., 10:1075–1081 (1972).
Kaplan, J., et al., Ann. Internal Med., 96(6):756–761 (1982).
Matsui, et al., J. Clin. Invest. 87:1456–1461 (1991).
Morse, D.L. et al., New Engl. J. Med., 314:678–681 (1986).
Murphy, A.N., et al., Med. J. Aust., 2:329–333 (1979).
Peptide Protein and Gene Technology, No. 6, Cambridge Research Biochemicals, Wilmington, Del.
Sekine, S., et al., Microbiol. Immunol., 33:207–217 (1989).
Thornhill, T.S., et al., J. Infect. Dis., 132:28–34 (1975).
Wilde, J., et al., J. Clin. Microbiol., 28(6):1300–1307 (1990).
Wilson, R., et al., Am. J. Public Health, 72:72–74 (1982).

| Test Clone | Patient Stool Sample | | | | Hybridization Temperature |
|---|---|---|---|---|---|
| | 1b | 2b | 1a | 2a | |
| pUC-27 | · | ● | · | ● | 50° |
| | | · | | ● | 65° |
| pUC-593 | ● | · | | ● | 50° |
| | ● | | | ● | 65° |
| pUC-13 | ● | ● | · | ● | 50° |
| | | · | | ● | 65° |
| pUCNV-953 | | · | ● | ● | 50° |
| | | | | | 65° |

Fig. 2A

```
                                        21                                    41
  G  TGC TCT GGG AGC GGG CAT ACA GGT TGG TGG CGA CAG GCC CTC CAA
     cys ser gly ser gly his thr gly trp trp arp gln ala leu gln 61                            81
     AGC CAA AGG TAT CAA CAA AAT TTG CAA CTG CAA GAA AAT TCT TTT
     ser gln arg tyr gln gln asn leu gln leu gln glu asn ser phe 101                        121
     AAA CAT GAC AGG GAA ATG ATT GGG TAT CAG GTT GAA GCT TCA AAT
     lys his asp arg glu met ile gly tyr gln val glu ala ser asn 141                        161                        18
     CAA TTA TTG GCT AAA AAT TTG GCA ACT AGA TAT TCA CTC CTC CGT
     gln leu leu ala lys asn leu ala thr arg tyr ser leu leu arg 1                        201                        221
     GCT GGG GGT TTG ACC AGT GCT GAT GCA GCA AGA TCT GTG GCA GGA
     ala gly gly leu thr ser ala asp ala ala arg ser val ala gly 241                            261
     GCT CCA GTC ACC CGC ATT GTA GAT TGG AAT GGC GTG AGA GTG TCT
     ala pro val thr arg ile val asp trp asn gly val arg val ser 281                        301
     GCT CCC GAG TCC TCT GCT ACC ACA TTG AGA TCC GGT GGC TTC ATG
     ala pro glu ser ser ala thr thr leu arg ser gly gly phe met 321                        341                        36
     TCA GTT CCC ATA CCA TTT GCC TCT AAG CAA AAA CAG GTT CAA TCA
     ser val pro ile pro phe ala ser lys gln lys gln val gln ser 1                    381                        401
     TCT GGT ATT AGT AAT CCA AAT TAT TCC CCT TCA TCC ATT TCT CGA
     ser gly ile ser asn pro asn tyr ser pro ser ser ile ser arg 421                        441
     ACC ACT AGT TGG GTC GAG TCA CAA AAC TCA TCG AGA TTT GGA AAT
     thr thr ser trp val glu ser gln asn ser ser arg phe gly asn 461                        481
     CTT TCT CCA TAC CAC GCG GAG GCT CTC AAT ACA GTG TGG TTG ACT
     leu ser pro tyr his ala glu ala leu asn thr val trp leu thr 501
     CCA CCC GGT TCA ACC
     pro pro gly ser thr
```

Fig. 5

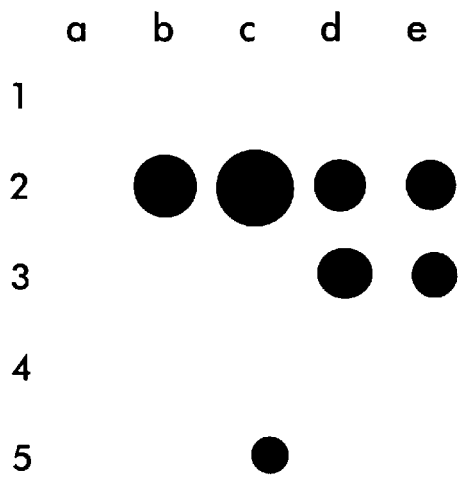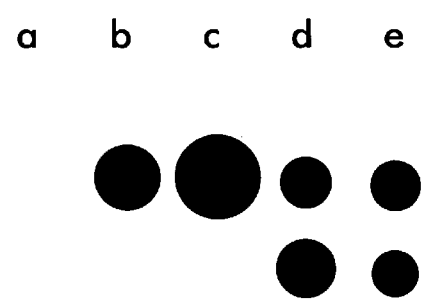
Fig. 7

```
NV    HFDADYTAWDSTQNRQIMT-ESFSIMSR---LTASPEL-AEVVAQDLLAPSEMDV------GDYVIRVK--EG-LPSGFPCTSQVN
HEV   VFENDFSEFDSTQNNFSLG-LECAIMEEC-GMPQWLI-RLYHLIRSAWILQAPKESLR--GFWKKH---S-KHSGEPGTLLWN
HCV   GFSYDTRCFDSTVTESDIR-TEEAIYQCCDLDPQARV-AIKSLTERLYVGGPLTNSR--GENCGYRRCRAS-RASGVLTSCGN
HAV   GLDLDFSAFDASLSPFMIREAGRIMSELS-GTPSHFGTALINTIIYSKHLLYNCCYHVCGS-----MPSGSPCTALLN
JE    MYADDTAGWDTRITRTDLE-NEAKVLELLDGEHRMLARAIIELTYRHKVKVMRPAAE-GKTVMDVISREDQRGSGQVVTYALN
POLIO FA-FDYTGYDASLS-PAWFEAL-KMVLEKIGFGDRVDY-IDYLNHSHHLYKNKTYCVKGG-----MPSGCSGTSIFN
FMD   VWDVDYSAFDANHCSDAMNIFEEVFRTDFGFHPNAEWILKTLVNTEHAYENKRITV-EGG-----MPSGCAATSMLN
EMC   VYDVDYSNFDSTHSVAMFRLLAEEFFTPENGF-DPLTREYLESLAISTHAFEEKRFLITGG------LPSGCAATSMLN
SNBV  VLETBIASFDKS-QDDAMALTGLMIEDL-GVDQPLLDLIECAFGEISSTHLPTGTRFKFGA--M------MKSLGMFLILFVN
TMV   VLELDISKYDKS-QNEFHCAVEYEIWRRL-GFEDFLGEVWKQG--HRKTTLK-DITA--GYKTC--IWY---QRKSGDVTFIGN
AMV   FKEIDFSKFDKS-QNELHHLIQERFLKYL-GIPNEFLTLVFNA--HRKSRIS-DSKN--GVFFN-VDF----QRRTGDALTYLGN
BMV   FLEADLSKFDKS-QGELHLEFQREILLAL-GFPAPLTNWWSDF--HRDSYLS-DPHAKVGMS-----VSF----QRRTGDAFTYFGN
CpMV  VLCCDYSSFDGLLSKQVMDVIASMINELCGGE-DQLKNARRNLLMACCSRLAICKNTVWRVECG------IPSGFPMTVIVN

NV    SINHWIITLCALSEATGLSPD------------------VVQSMSYFSFYGDDEIVS----TDIDFDP-ARLTQILK--E
HEV   TVWNMAVITHC---------------------YDFRDFQVAAFKGDDSIVL--CSEYRQSPG--A-A--VLIAGC
HCV   TLTCYIKARAACRAAGLQDCTMLVC-----------------CESAGVQED---A--SL--RAF
HAV   SIINNVNLYYVFSKI-----------FGKSPVFFCQALKILCYGDDVLIV--FSRDVQIDNLDLIGQKTVDEF
JE    TFTNIAVQLVRLMEAEGVIGPQHLEQLPRKTKIAVRTWLFENGEERVTRMAISGDDCVVK----PLDDRFATALHFL--NAM
POLIO SMINNLIIRTLLLKTYKGID---------------LDHLKMIAYGDDVIAS---YPHEVDAS-----LAQS
FMD   TILNNIYVLYALRRHYEGVE----------------LDTYTMISYGDDIVVA----SDYDLDF---EALKP--H
EMC   TIMNNIIIRAGLYLTYKNFE----------------FDDVKVLSYGDDLLVA--TNYQLDFDKV--RASLAKTG
SNBV  TVLNVVIASRVLE-------------ERLKTSRCAAFIGDDNIIH---GVVSDKEMAERCATWL-N
TMV   TVIIAACLASML--------------PMEKIIKGAFCGDDSLLY--FPKGCEFPDVQHSAN-LMWNFE
AMV   TIVTLACLCHVYDLM------------DPNVKFVVASGDDSLIG---TVEELPRDQEF-LFTTLFNLE
BMV   TLVTMAMIAYASDLS------------DCDCAIFSGDDSLII--SKVKPVLDTDM--FTSLFNME
CpMV  SIFNEILIRYHYKKLMREQQAPE-----------LMVQSFDKLIGLVTYGDDNLISVNAVVTPYFDGKKL-KQSLAQGG

Fig. 8
```

POLYCLONAL AND MONOCLONAL ANTIBODIES TO NORWALK VIRUS AND METHODS FOR MAKING THEM

This application is a continuation of prior U.S. application Ser. No. 07/573,509, filed on Aug. 27, 1990, now abandoned, which was a continuation-in-part of both U.S. application Ser. No. 07/515,993, filed Apr. 27, 1990, now abandoned, and U.S. application Ser. No. 07/433,492, filed Nov. 8, 1989, now abandoned.

This application is Continuation-in-Part of Applicant's Co-Pending U.S. application Ser. No. 07/433,492 filed Nov. 8, 1989, entitled "Methods and Reagents to Detect and Characterize Norwalk and Related Viruses."

This invention is supported in part through a grant or award from the Food and Drug Administration.

FIELD OF THE INVENTION

The present invention relates generally to synthesizing clones of Norwalk virus and to making probes to Norwalk and related viruses. It also relates to methods of detection and characterization of Norwalk and related viruses.

BACKGROUND OF THE INVENTION

Norwalk virus is one of the most important viral pathogens causing acute gastroenteritis, the second most common illness in the United States (Dingle et al., 1953; Kapikian and Chanock, 1985). Up to 42% of cases of viral gastroenteritis have been estimated to be caused by Norwalk or Norwalk-like viruses (Kaplan et al., 1982). Both water and foodborne transmission of Norwalk virus has been documented, and particularly large epidemic outbreaks of illness have occurred following consumption of contaminated shellfish including clams, cockles, and oysters (Murphy et al., 1979; Gunn et al., 1982; Wilson et al., 1982; Gill et al., 1983; DuPont 1986; Morse et al., 1986; Sekine et al., 1989). An increase in fish and shellfish-related food poisonings has recently been noted and attributed to increased recognition of these entities by clinicians as well as to increased consumption of seafood (Eastaugh and Shepherd, 1989). Norwalk virus was discovered in 1973. However, knowledge about the virus has remained limited because it has failed to grow in cell cultures and no suitable animal models have been found for virus cultivation. Human stool samples obtained from outbreaks and from human volunteer studies, therefore, are the only source of the virus. Still the concentration of the virus in stool is usually so low that virus detection with routine electron microscopy is not possible (Dolin et al., 1972; Kapikian et al., 1972; Thornhill et al., 1975). Current methods of Norwalk virus detection include immune electron microscopy and other immunologic methods such as radio immunoassays (RIAs) or a biotin-avidin enzyme linked immunoabsorbent assays (ELISAs) which utilize acute and convalescent phase serum from humans. To date, no hyperimmune serum from animals has been successfully prepared due either to insufficient quantities or unusual properties of the viral antigen. Preliminary biophysical characterization of virions has indicated particles contain one polypeptide (Greenberg et al., 1981), but efforts to characterize the viral genome have failed. Therefore, these viruses have remained unclassified.

CITED AND RELEVANT INFORMATION

1. Dingle J, Badger G, Feller A et al. 1953. A study of illness in a group of Cleveland families: 1. Plan of study and certain general observations. Am. J. Hyg. 58:16–30.

2. Dolin R, Blacklow N R, DuPont H, Buscho R F, Wyatt R G, Kasel J A, Hornick R, and Chanock R M. 1972. Biological properties of Norwalk agent of acute infectious nonbacterial gastroenteritis. Proc. Soc. Exp. Med. and Biol. 140:578–583.

3. Dolin R, Blacklow N R, DuPont H, Formal S, Buscho R F, Kasel J A, Chames R P, Hornick R, and Chanock R M. 1971. Transmission of acute infectious nonbacterial gastroenteritis to volunteers by oral administration of stool filtrates. J. Infect. Dis. 123:307–312.

4. DuPont H L. 1986. Consumption of raw shellfish—is the risk now unacceptable? New Engl. J. Med. 314:707–708.

5. Eastaugh J, Shepherd S. 1989. Infectious and toxic syndromes from fish and shellfish consumption. Arch. Intern. Med. 149:1735–1740.

6. Gill O N, Cubitt W D, McSwiggan D A, Watney B M and Bartlett C L R. 1983. Epidemic of gastroenteritis caused by oysters contaminated with small round structured viruses. Br. Med. J. 287:1532–1534.

7. Greenberg H B, Valdesuso J R, Kalica A R, Wyatt R G, McAuliffe V J, Kapikian A Z and Chanock R M. 1981. Proteins of Norwalk virus. J. Virol. 37: 994–999.

8. Gunn R A, Janowski H T, Lieb S, Prather E C, and Greenberg H B. 1982. Norwalk virus gastroenteritis following raw oyster consumption. Am. J. Epidemiol. 115:348–351.

9. Jiang X, Estes M K, and Metcalf T G. 1989. In situ hybridization for quantitative assay of infectious hepatitis A virus. J. Clin. Microbiol. 27:874–879.

10. Jiang X, Estes M K, and Metcalf T G. 1987. Detection of hepatitis A virus by hybridization with single-stranded RNA probes. Appl. Environ. Microbiol. 53:2487–2495.

11. Jiang X, Estes M K, Metcalf T G, and Melnick J L. 1986. Detection of hepatitis A virus in seeded estuarine samples by hybridization with cDNA probes. Appl. Environ. Microbiol. 52:711–717.

12. Kapikian A Z and Chanock R M. 1990. Norwalk group of viruses. In: BN Fields (ed.) Virology, Raven Press, New York, pp. 671–693.

13. Kapikian A Z, Wyatt R G, Dolin R, Thornhill T S, Kalica A R, and Chanock R M. 1972. Visualization by immune electron microscopy of a 27-nm particle associated with acute infectious nonbacterial gastroenteritis. J. Virol. 10:1075–1081.

14. Kaplan J, Feldman R, Campbell D et al. 1982. Epidemiology of Norwalk Gastroenteritis and the Role of Norwalk Virus in Outbreaks of Acute Nonbacterial Gastroenteritis. Ann. Internal Med. 96(6): 756–761.

15. Morse D L, Guzewich J J, Hanrahan J P, Stricof R, Shayegani M, Deibel R, Grabau J C, Nowak N A, Herrmann J E, Cukor G, and Blacklow N R. 1986. Widespread outbreaks of clam- and oyster-associated gastroenteritis: role of Norwalk virus. New Engl. J. Med. 314:678–681.

16. Murphy A M, Grohmann G S, Christopher P J, Lopez W A, Davey G R, and Millsom R H. 1979. An Australia-wide outbreak of gastroenteritis from oysters caused by Norwalk virus. Med. J. Aust. 2:329–333.

17. Sekine S, Okada S, Hayashi Y, Ando T, Terayama T, Yabuuchi K, Miki T, and Ohashi M. 1989. Prevalence of small round structured virus infections in acute gastroenteritis outbreaks in Tokyo. Microbiol. Immunol. 33:207–217.

18. Thornhill T S, Kalica A R, Wyatt R G, Kapikian A Z, and Chanock R M. 1975. Pattern of shedding of the Norwalk particle in stools during experimentally induced gastroenteritis in volunteers as determined by immune electron microscopy. J. Infect. Dis. 132:28–34.
19. Wilson R, Anderson L J, Holman R C, Gary G W, and Greenberg H B. 1982. Waterborne gastroenteritis due to the Norwalk agent: clinical and epidemiologic investigation. Am. J. Public Health 72:72–74.
20. Hayashi Y, Ando T, Utagawa E, Sekine S, Okada S, Yabuuchi K, Miki T, and Ohashi M. 1989. Western Blot (Immunoblot) Assay, Round-Structured Virus Associated with an Acute Gastroenteritis Outbreak in Tokyo. J. Clin. Microbiol. 27:1728–1733.
21. U.S. Pat. No. 4,358,535, issued Nov. 9, 1982, to Fahkow S and Moseley S L. Specific DNA Probes in Diagnostic Microbiology.
22. U.S. Pat. No. 4,751,080, issued Jun. 14, 1988, to Wyatt R G, Kapikian A Z, Chanock R M, Midthum K, Flores J, Hoshino Y. Vaccine Against Rotavirus Diseases.
23. U.S. Pat. No. 4,814,268, issued Mar. 21, 1989, to Kreider J W and Howett M. K. Methods for Propagating Fastidious Human Viruses and for Producing Purified Suspensions Thereof.

SUMMARY OF THE INVENTION

It is therefore an object of the invention to characterize the Norwalk and related virus genomes by synthesizing and cloning a cDNA library.

It is an associated object of the invention to deduce an amino acid sequence of cDNA.

Another object of the invention is to develop a method of preparing polyclonal and monoclonal antibodies to the Norwalk and related viruses.

Still another object of the invention is to develop a method of making probes to detect Norwalk and related viruses.

A further object of the invention is to use the cDNA or fragments or derivatives thereof in assays to detect Norwalk and related viruses in samples suspected of containing the viruses.

A nucleotide sequence of the genome sense strand of a fragment of the Norwalk virus cDNA clone according to the presently preferred embodiment of the invention intended to accomplish the foregoing objects includes:

```
GGCGTCAAAA GACGTCGTTC CTACTGCTGC TAGCAGTGAA    40
AATGCTAACA ACAATAGTAG TATTAAGTCT CGTCTATTGG    80
CGAGACTCAA GGGTTCAGGT GGGGCTACGT CCCCACCCAA   120
CTCGATAAAG ATAACCAACC AAGATATGGC TCTGGGCTG    160
ATTGGACAGG TCCCAGCGCC AAAGGCCACA TCCGTCGATG   200
TCCCTAAACA ACAGAGGGAT AGACCACCAC GGACTGTTGC   240
CGAAGTTCAA CAAAATTTGC GTTGGACTGA GAGACCACAA   280
GACCAGAATG TTAAGACGTG GGATGAGCTT GACCACACAA   320
CAAAACAACA GATACTTGAT GAACACGCTG AGTGGTTTGA   360
TGCCGGTGGC TTAGGTCCAA GTACACTACC CACTAGTCAT   400
```

-continued
```
GAACGGTACA CACATGAGAA TGATGAAGGC CACCAGGTAA    440
AGTGGTCGGC TAGGGAAGGT GTAGACCTTG GCATATCCGG    480
GCTCACGACG GTGTCTGGGC CTGAGTGGAA TATGTGCCCG    520
CTACCACCAG TTGACCAAAG GAGCACGACA CCTGCAACTG    560
AGCCCACAAT TGGTGACATG ATCGAATTCT ATGAAGGGCA    600
CATCTATCAT TATGCTATAT ACATAGGTCA AGGCAAGACG    640
GTGGGTGTAC ACTCCCCTCA AGCAGCCTTC TCAATAACGA    680
GGATCACCAT ACAGCCCATA TCAGCTTGGT GGCGAGTCTG    720
TTATGTCCCA CAACCAAAAC AGAGGCTCAC ATACGACCAA    760
CTCAAAGAAT TAGAAAATGA ACCATGGCCG TATGCCGCAG    800
TCACGAACAA CTGCTTCGAA TTTTGTTGCC AGGTCATGTG    840
CTTGGAAGAT ACTTGGTTGC AAAGGAAGCT CATCTCCTCT    880
GGCCGGTTTT ACCACCCGAC CCAAGATTGG TCCCGAGACA    920
CTCCAGAATT CCAACAAGAC AGCAAGTTAG AGATGGTTAG    960
GGATGCAGTG CTAGCCGCTA TAAATGGGTT GGTGTCGCGG   1000
CCATTTAAAG ATCTTCTGGG TAAGCTCAAA CCCTTGAACG   1040
TGCTTAACTT ACTTTCAAAC TGTGATTGGA CGTTCATGGG   1080
GGTCGTGGAG ATGGTGGTCC TCCTTTTAGA ACTCTTTGGA   1120
ATCTTTTGGA ACCCACCTGA TGTTTCCAAC TTTATAGCTT   1160
CACTCCTGCC AGATTTCCAT CTACAGGGCC CCGAGGACCT   1200
TGCCAGGGAT CTCGTGCCAA TAGTATTGGG GGGGATCCGC   1240
TTAGCCATAG GATTCACCAG AGACAAGGTA AGTAAGATGA   1280
TGAAGAATGC TGTTGATGGA CTTCGTGCGG CAACCCAGCT   1320
CGGTCAATAT GGCCTAGAAA TATTCTCATT ACTAAAGAAG   1360
TACTTCTTCG GTGGTGATCA AACAGAGAAA ACCCTAAAAG   1400
ATATTGAGTC AGCAGTTATA GATATGGAAG TACTATCATC   1440
TACATCAGTG ACTCAGCTCG TGAGGGACAA ACAGTCTGCA   1480
CGGGCTTATA TGGCCATCTT AGATAATGAA GAAGAAAAGG   1520
CAAGGAAATT ATCTGTCAGG AATGCCGACC CACACGTAGT   1560
ATCCTCTACC AATGCTCTCA TATCCCGGAT CTCAATGGCT   1600
AGGGCTGCAT TGGCCAAGGC TCAAGCTGAA ATGACCAGCA   1640
GGATGCGTCC TGTGGTCATT ATGATGTGTG GGCCCCCTGG   1680
TATAGGTAAA ACCAAGGCAG CAGAACATCT GGCTAAACGC   1720
CTAGCCAATG AGATACGGCC TGGTGGTAAG GTTGGGCTGG   1760
TCCCACGGGA GGCAGTGGAT CATTGGGATG GATATCACGG   1800
AGAGGAAGTG ATGCTGTGGG ACGACTATGG AATGACAAAG   1840
ATACAGGAAG ACTGTAATAA ACTGCAAGCC ATAGCCGACT   1880
CAGCCCCCCT AACACTCAAT TGTGACCGAA TAGAAAACAA   1920
GGGAATGCAA TTTGTGTCTG ATGCTATAGT CATCACCACC   1960
AATGCTCCTG GCCCAGCCCC AGTGGACTTT GTCAACCTCG   2000
```

```
                                -continued
GGCCTGTTTG CCGAAGGGTG GACTTCCTTG TGTATTGCAC   2040
GGCACCTGAA GTTAACACA CGAGGAAAGT CAGTCCTGGG   2080
GACACAACTG CACTGAAAGA CTGCTTCAAG CCCGATTTCT   2120
CACATCTAAA AATGGAGTTG GCTCCCCAAG GGGGCTTTGA   2160
TAACCAAGGG AATACCCCGT TTGGTAAGGG TGTGATGAAG   2200
CCCACCACCA TAAACAGGCT GTTAATCCAG GCTGTAGCCT   2240
TGACGATGGA GAGACAGGAT GAGTTCCAAC TCCAGGGGCC   2280
TACGTATGAC TTTGATACTG ACAGAGTAGC TGCGTTCACG   2320
AGGATGGCCC GAGCCAACGG GTTGGGTCTC ATATCCATGG   2360
CCTCCCTAGG CAAAAAGCTA CGCAGTGTCA CCACTATTGA   2400
AGGATTAAAG AATGCTCTAT CAGGCTATAA AATATCAAAA   2440
TGCAGTATAC AATGGCAGTC AAGGGTGTAC ATTATAGAAT   2480
CAGATGGTGC CAGTGTACAA ATCAAAGAAG ACAAGCAAGC   2520
TTTGACCCCT CTGCAGCAGA CAATTAACAC GGCCTCACTT   2560
GCCATCACTC GACTCAAAGC AGCTAGGGCT GTGGCATACG   2600
CTTCATGTTT CCAGTCCGCC ATAACTACCA TACTACAAAT   2640
GGCGGGATCT GCGCTCGTTA TTAATCGAGC GGTCAAGCGT   2680
ATGTTTGGTA CCCGTACAGC AGCCATGGCA TTAGAAGGAC   2720
CTGGGAAAGA ACATAATTGC AGGGTCCATA AGGCTAAGGA   2760
AGCTGGAAAG GGGCCCATAG GTCATGATGA CATGGTAGAA   2800
AGGTTTGGCC TATGTGAAAC TGAAGAGGAG GAGAGTGAGG   2840
ACCAAATTCA AATGGTACCA AGTGATGCCG TCCCAGAAGG   2880
AAAGAACAAA GGCAAGACCA AAAAGGGACG TGGTCGCAAA   2920
AATAACTATA ATGCATTCTC TCGCCGTGGT CTGAGTGATG   2960
AAGAATATGA AGAGTACAAA AAGATCAGAG AAGAAAAGAA   3000
TGGCAATTAT AGTATACAAG AATACTTGGA GGACCGCCAA   3040
CGATATGAGG AAGAATTAGC AGAGGTACAG GCAGGTGGTG   3080
ATGGTGGCAT AGGAGAAACT GAAATGGAAA TCCGTCACAG   3120
GGTCTTCTAT AAATCCAAGA GTAAGAAACA CCAACAAGAG   3160
CAACGGCGAC AACTTGGTCT AGTGACTGGA TCAGACATCA   3200
GAAAACGTAA GCCCATTGAC TGGACCCCGC CAAAGAATGA   3240
ATGGGCAGAT GATGACAGAG AGGTGGATTA TAATGAAAAG   3280
ATCAATTTTG AAGCTCCCCC GACACTATGG AGCCGAGTCA   3320
CAAAGTTTGG ATCAGGATGG GGCTTTTGGG TCAGCCCGAC   3360
AGTGTTCATC ACAACCACAC ATGTAGTGCC AACTGGTGTG   3400
AAAGAATTCT TTGGTGAGCC CCTATCTAGT ATAGCAATCC   3440
ACCAAGCAGG TGAGTTCACA CAATTCAGGT TCTCAAAGAA   3480
AATGCGCCCT GACTTGACAG GTATGGTCCT TGAAGAAGGT   3520
TGCCCTGAAG GGACAGTCTG CTCAGTCCTA ATTAAACGGG   3560
ATTCGGGTGA ACTACTTCCG CTAGCCGTCC GTATGGGGGC   3600
TATTGCCTCC ATGAGGATAC AGGGTCGGCT TGTCCATGGC   3640
CAATCAGGGA TGTTACTGAC AGGGGCCAAT GCAAAGGGGA   3680
TGGATCTTGG CACTATACCA GGAGACTGCG GGGCACCATA   3720
CGTCCACAAG CGCGGGAATG ACTGGGTTGT GTGTGGAGTC   3760
CACGCTGCAG CCACAAAGTC AGGCAACACC GTGGTCTGCG   3800
CTGTACAGGC TGGAGAGGGC GAAACCGCAC TAGAAGGTGG   3840
AGACAAGGGG CATTATGCCG GCCACGAGAT TGTGAGGTAT   3880
GGAAGTGGCC CAGCACTGTC AACTAAAACA AAATTCTGGA   3920
GGTCCTCCCC AGAACCACTG CCCCCCGGAG TATATGAGCC   3960
AGCATACCTG GGGGGCAAGG ACCCCCGTGT ACAGAATGGC   4000
CCATCCCTAC AACAGGTACT ACGTGACCAA CTGAAACCCT   4040
TTGCGGACCC CCGCGGCCGC ATGCCTGAGC CTGGCCTACT   4080
GGAGGCTGCG GTTGAGACTG TAACATCCAT GTTAGAACAG   4120
ACAATGGATA CCCCAAGCCC GTGGTCTTAC GCTGATGCCT   4160
GCCAATCTCT TGACAAAACT ACTAGTTCGG GGTACCCTCA   4200
CCATAAAAGG AAGAATGATG ATTGGAATGC CACCACCTTC   4240
GTTGGAGAGC TCGGTGAGCA AGCTGCACAC GCCAACAATA   4280
TGTATGAGAA TGCTAAACAT ATGAAACCCA TTTACACTGC   4320
AGCCTTAAAA GATGAACTAG TCAAGCCAGA AAAGATTTAT   4360
CAAAAAGTCA AGAAGCGTCT ACTATGGGGC GCCGATCTCG   4400
GAACAGTGGT CAGGGCCGCC CGGGCTTTTG GCCCATTTTG   4440
TGACGCTATA AAATCACATG TCATCAAATT GCCAATAAAA   4480
GTTGGCATGA ACACAATAGA AGATGGCCCC CTCATCTATG   4520
CTGAGCATGC TAAATATAAG AATCATTTTG ATGCAGATTA   4560
TACAGCATGG GACTCAACAC AAAATAGACA AATTATGACA   4600
GAATCCTTCT CCATTATGTC GCGCCTTACG GCCTCACCAG   4640
AATTGGCCGA GGTTGTGGCC CAAGATTTGC TAGCACCATC   4680
TGAGATGGAT GTAGGTGATT ATGTCATCAG GGTCAAAGAG   4720
GGGCTGCCAT CTGGATTCCC ATGTACTTCC AGGTGAACA   4760
GCATAAATCA CTGGATAATT ACTCTCTGTG CACTGTCTGA   4800
GGCCACTGGT TTATCACCTG ATGTGGTGCA ATCCATGTCA   4840
TATTTCTCAT TTTATGGTGA TGATGAGATT GTGTCAACTG   4880
ACATAGATTT TGACCCAGCC CGCCTCACTC AAATTCTCAA   4920
GGAATATGGC CTCAAACCAA CAAGGCCTGA CAAAACAGAA   4960
GGACCAATAC AAGTGAGGAA AAATGTGGAT GGACTGGTCT   5000
TCTTGCGGCG CACCATTTCC CGTGATGCGG CAGGGTTCCA   5040
AGGCAGGTTA GATAGGGCTT CGATTGAACG CCAAATCTTC   5080
TGGACCCGCG GGCCCAATCA TTCAGATCCA TCAGAGACTC   5120
TAGTGCCACA CACTCAAAGA AAAATACAGT TGATTTCACT   5160
TCTAGGGGAA GCTTCACTCC ATGGTGAGAA ATTTTACAGA   5200
```

```
-continued
AAGATTTCCA GCAAGGTCAT ACATGAAATC AAGACTGGTG    5240

GATTGGAAAT GTATGTCCCA GGATGGCAGG CCATGTTCCG    5280

CTGGATGCGC TTCCATGACC TCGGATTGTG GACAGGAGAT    5320

CGCGATCTTC TGCCCGAATT CGTAAATGAT GATGCGTCTA    5360
                                         **
AGGACGCTAC ATCAAGCGTG GATGGCGCTA GTGGCGCTGG    5400

TCAGTTGGTA CCGGAGGTTA ATGCTTCTGA CCCTCTTGCA    5440

ATGGATCCTG TAGCAGGTTC TTCGACAGCA GTCGCGACTG    5480

CTGGACAAGT TAATCCTATT GATCCCTGGA TAATTAATAA    5520

TTTTGTGCAA GCCCCCAAG GTGAATTTAC TATTTCCCCA     5560

AATAATACCC CCGGTGATGT TTTGTTTGAT TTGAGTTTGG    5600

GTCCCCATCT TAATCCTTTC TTGCTCCATC TATCACAAAT    5640

GTATAATGGT TGGGTTGGTA ACATGAGAGT CAGGATTATG    5680

CTAGCTGGTA ATGCCTTTAC TGCGGGGAAG ATAATAGTTT    5720

CCTGCATACC CCCTGGTTTT GGTTCACATA ATCTTACTAT    5760

AGCACAAGCA ACTCTCTTTC CACATGTGAT TGCTGATGTT    5800

AGGACTCTAG ACCCCATTGA GGTGCCTTTG GAAGATGTTA    5840

GGAATGTTCT CTTTCATAAT AATGATAGAA ATCAACAAAC    5880

CATGCGCCTT GTGTGCATGC TGTACACCCC CCTCCGCACT    5920

GGTGGTGGTA CTGGTGATTC TTTTGTAGTT GCAGGGCGAG    5960

TTATGACTTG CCCCAGTCCT GATTTTAATT TCTTGTTTTT    6000

AGTCCCTCCT ACGGTGGAGC AGAAAACCAG GCCCTTCACA    6040

CTCCCAAATC TGCCATTGAG TTCTCTGTCT AACTCACGTG    6080

CCCCTCTCCC AATCAGTAGT ATGGGCATTT CCCCAGACAA    6120

TGTCCAGAGT GTGCAGTTCC AAAATGGTCG GTGTACTCTG    6160

GATGGCCGCC TGGTTGGCAC CACCCCAGTT TCATTGTCAC    6200

ATGTTGCCAA GATAAGAGGG ACCTCCAATG GCACTGTAAT    6240

CAACCTTACT GAATTGGATG GCACACCCTT TCACCCTTTT    6280

GAGGGCCCTG CCCCCATTGG GTTTCCAGAC CTCGGTGGTT    6320

GTGATTGGCA TATCAATATG ACACAGTTTG GCCATTCTAG    6360

CCAGACCCAG TATGATGTAG ACACCACCCC TGACACTTTT    6400

GTCCCCCATC TTGGTTCAAT TCAGGCAAAT GGCATTGGCA    6440

GTGGTAATTA TGTTGGTGTT CTTAGCTGGA TTTCCCCCCC    6480

ATCACACCCG TCTGGCTCCC AAGTTGACCT TTGGAAGATC    6520

CCCAATTATG GGTCAAGTAT TACGGAGGCA ACACATCTAG    6560

CCCCTTCTGT ATACCCCCT GGTTTCGGAG AGGTATTGGT     6600

CTTTTTCATG TCAAAAATGC CAGGTCCTGG TGCTTATAAT    6640

TTGCCCTGTC TATTACCACA AGAGTACATT TCACATCTTG    6680

CTAGTGAACA AGCCCCTACT GTAGGTGAGG CTGCCCTGCT    6720

CCACTATGTT GACCCTGATA CCGGTCGGAA TCTTGGGGAA    6760

TTCAAAGCAT ACCCTGATGG TTTCCTCACT TGTGTCCCCA    6800
```

```
-continued
ATGGGGCTAG CTCGGGTCCA CAACAGCTGC CGATCAATGG    6840

GGTCTTTGTC TTTGTTTCAT GGGTGTCCAG ATTTTATCAA    6880

TTAAAGCCTG TGGGAACTGC CAGCTCGGCA AGAGGTAGGC    6920

TTGGTCTGCG CCGATAATGG CCCAAGCCAT AATTGGTGCA    6960

ATTGCTGCTT CCACAGCAGG TAGTGCTCTG GGAGCGGGCA    7000

TACAGGTTGG TGGCGACAGG CCCTCCAAAG CCAAAGGTAT    7040

CAACAAAATT TGCAACTGCA AGAAAATTCT TTTAAACATG    7080

ACAGGGAAAT GATTGGGTAT CAGGTTGAAG CTTCAAATCA    7120

ATTATTGGCT AAAAATTTGG CAACTAGATA TTCACTCCTC    7160

CGTGCTGGGG GTTTGACCAG TGCTGATGCA GCAAGATCTG    7200

TGGCAGGAGC TCCAGTCACC CGCATTGTAG ATTGGAATGG    7240

CGTGAGAGTG TCTGCTCCCG AGTCCTCTGC TACCACATTG    7280

AGATCCGGTG GCTTCATGTG AGTTCCCATA CCATTTGCCT    7320

CTAAGCAAAA ACAGGTTCAA TCATCTGGTA TTAGTAATCC    7360

AAATTATTCC CCTTCATCCA TTTCTCGAAC CACTAGTTGG    7400

GTCGAGTCAC AAAACTCATC GAGATTTGGA AATCTTTCTC    7440

CATACCACGC GGAGGCTCTC AATACAGTGT GGTTGACTCC    7480

ACCCGGTTCA ACAGCCTCTT CTACACTGTC TTCTGTGCCA    7520

CGTGGTTATT TCAATACAGA CAGGTTGCCA TTATTCGCAA    7560

ATAATAGGCG ATGATGTTGT AATATGAAAT GTGGGCATCA    7600

TATTCATTTA ATTAGGTTTA ATTAGGTTTA ATTTGATGTT    7640

AAAAAAAAAA AAAAAAAAAA AAAAAAAAAA AAAAAAAAA     7680

AAAAAAAAAA AAAAAAAAAA AAAAAAAAAA AAAAAAAAA     7720

AA                                              7722
```

Within the above nucleotide sequence is a region where a RNA-dependent RNA polymerase is found. The RNA-dependent RNA polymerase is between bases 4543 and 4924 of the nucleotide sequence of the genome. The RNA polymerase and the corresponding oligopeptide include:

```
CAT TTT GAT GCA GAT TAT ACA GCA TGG GAC TCA ACA CAA AAT
HIS PHE ASP ALA ASP TYR THR ALA TRP ASP SER THR GLN ASN
            5                       10

AGA CAA ATT ATG ACA GAA TCC TTC TCC ATT ATG TCG CGC CTT
ARG GLN ILE MET THR GLU SER PHE SER THR MET SER ARG LEU
15                  20                  25

ACG GCC TCA CCA GAA TTG GCC GAG GTT GTG GCC CAA GAT TTG
THR ALA SER PRO GLU LEU ALA GLU VAL VAL ALA GLN ASP LEU
        30                  35                  40

CTA GCA CCA TCT GAG ATG GAT GTA GGT GAT TAT GTC ATC AGG
LEU ALA PRO SER GLU MET ASP VAL GLY ASP TYR VAL ILE ARG
            50                  55                  60

GTC AAA GAG GGG CTG CCA TCT GGA TTC CCA TGT ACT TCC CAG
VAL LYS GLU GLY LEU PRO SER GLY PHE PRO CYS THR SER GLN
                65                  70                  75

GTG AAC AGC ATA AAT CAC TGG ATA ATT ACT CTC TGT GCA CTG
VAL ASN SER ILE ASN HIS TRP ILE ILE THR LEU CYS ALA LEU
                80                  85

TCT GAG GCC ACT GGT TTA TCA CCT GAT GTG GTG CAA TCC ATG
SER GLU ALA THR GLY LEU SER PRO ASP VAL VAL GLN SER MET
90                  95                  100

TCA TAT TTC TCA TTT TAT GGT GAT GAT GAG ATT GTG TCA ACT
SER TYR PHE SER PHE TYR GLY ASP ASP GLU ILE VAL SER THR
    105                 110                 115

GAC ATA GAT TTT GAC CCA GCC CGC CTC ACT CAA ATT CTC AAG GAA
ASP ILE ASP PHE ASP PRO ALA ARG LEU THR GLN ILE LEU LYS GLU
        120                 125                 130
```

This oligopeptide and other cDNAs representing the entire genome found with this cDNA, or other oligonucleotides or fragments of the entire cDNA, are used to make diagnostic products and vaccines.

Other and still further objects, features and advantages of the present invention will be apparent from the following description of a presently preferred embodiment of the invention.

BRIEF DESCRIPTION OF THE FIGURES

FIG. 1. EM picture of Norwalk viruses after CsCl gradient purification.

FIG. 2*a*. Hybridization of stool samples with $^{32}P$-labeled plasmid DNA for screening positive Norwalk cDNA clones. Nucleic acids from paired stools [before (b) and after (a) infection with Norwalk virus] from two volunteers (1 and 2) were dotted on Zetabind filters. Replicate strips were prepared and hybridized at 50° C. and 65° C. with each test clone (pUC-27, pUC-593, pUC-13 and pUCNV-953). One clone (pUCNV-953) which reacted only with stool samples after (but not before) Norwalk infection was considered as a potential positive clone and was chosen for further characterization.

FIG. 2*b*. Dot blot hybridization of clone $^{32}P$-labeled pUCNV-953 with another 3 sets of stool samples collected at different times after infection (B=before acute phase of illness; A=acute phase of illness; P=post-acute phase of illness) of 3 volunteers. The nucleic acids were dotted directly or after treatment with RNAse or with DNAse before dotting. Double-stranded homologous cDNA (pUCNV-953) was dotted after the same treatments as the stool samples.

FIG. 3. Dot blot hybridization of Norwalk viruses in a CsCl gradient with ssRNA probes made from pGEMNV-953. Aliquots of 50 ul from each fraction in a CsCl gradient were dotted onto a Zetabind filter. Duplicates of filters were made and hybridized with the two ssRNA probes respectively. The two strands were subsequently called cRNA (positive hybridization with the viral nucleic acid) and vRNA (no hybridization with the viral nucleic acid, data not shown). The graph shows EM counts of Norwalk viruses from each fraction of the same CsCl gradient for the dot blot hybridization. Five squares from each grid were counted and the average of the number of viral particles per square was calculated.

FIG. 4. Hybridization of Norwalk viral RNA with $^{32}P$-labeled clone pUCNV-953. Nucleic acids extracted from partially purified viruses were electrophoresed in a native agarose gel as described previously (Jiang et al., 1989). The gel was then dried at 80° C. for 1 h and hybridized with $^{32}P$-labeled pUCNV-953 insert. Lane 1, 23 S and 16 S rRNA from *E. coli* (Miles Laboratories Inc., Naperville, Ill. 60566), lanes 2 and 4, total nucleic acids from partially purified stool samples containing Norwalk virus, and lane 3, HAV RNA.

FIG. 5. The nucleotide sequence of the genome sense strand of the first Norwalk virus cDNA clone. The deduced amino acid sequence of a long open reading frame in this cDNA is also shown.

FIG. 6. Physical map of Norwalk virus specific clones isolated from the pUC-13 library. This map assumes the Norwalk genome is 8 kb and shows only a subset (the four largest) of ~100 characterized clones. cDNAs which represent at least 7 kb of nucleic acid have been identified by hybridization with pre-and post infected stool samples, or by rescreening the library with 5'-end probes of the original (pUCNV-953) and subsequent positive clones. A poly(A) tail (~80 bases) is present at the 3'-end of clone pUCNV-4145. Clone pUCNV-1011 also hybridized specifically with post- (but not pre-) infection stools from volunteers (see FIG. 7).

FIG. 7a. Dot blot hybridization of stool samples with $^{32}$P-labeled probes, derived from pUCNV-953, representing the 3'-end of the Norwalk viral genome. Stool samples were collected from 5 volunteers at different times (a–e) after infection with Norwalk virus. Samples in column (a) were collected in the first 24 h post-infection, before symptoms appeared. The rest of the stool samples were collected from day 2 to day 5 post-infection. Nucleic acids were extracted and duplicate dots were immobilized on a Zetabind filter.

FIG. 7b. Dot blot hybridization of stool samples with $^{32}$P-labeled probes, derived from pUCNV-1011, representing the 5'-end of the Norwalk viral genome. Stool samples were collected from 5 volunteers at different times (a–e) after infection with Norwalk virus. Samples in column (a) were collected in the first 24 h post-infection, before symptoms appeared. The rest of the stool samples were collected from day 2 to day 5 post-infection. Nucleic acids were extracted and duplicate dots were immobilized on a Zetabind filter.

FIG. 8. Norwalk virus encodes an RNA-directed RNA polymerase sequence motif. The deduced amino acid sequence of a portion of Norwalk virus pUCNV-4095 (NV) is compared with consensus amino acid residues thought to encode putative RNA-directed RNA polymerases of hepatitis E virus (HEV), hepatitis C virus (HCV), hepatitis A virus (HAV), Japanese encephalitis virus (JE), poliovirus (polio), foot-and-mouth disease virus (FMD), encephalomyocarditis virus (EMC), Sindbis virus (SNBV), tobacco mosaic virus (TMV), alfalfa mosaic virus (AMV), brome mosaic virus (BMV), and cowpea mosaic virus (CpMV). Sequences for viruses other than NV are from FIG. 3 of Reyes et al., Science 247:1335–1339.

FIG. 9. Three sets of primers used to amplify the Norwalk virus genome.

DETAILED DESCRIPTION OF THE INVENTION

Figure 1:
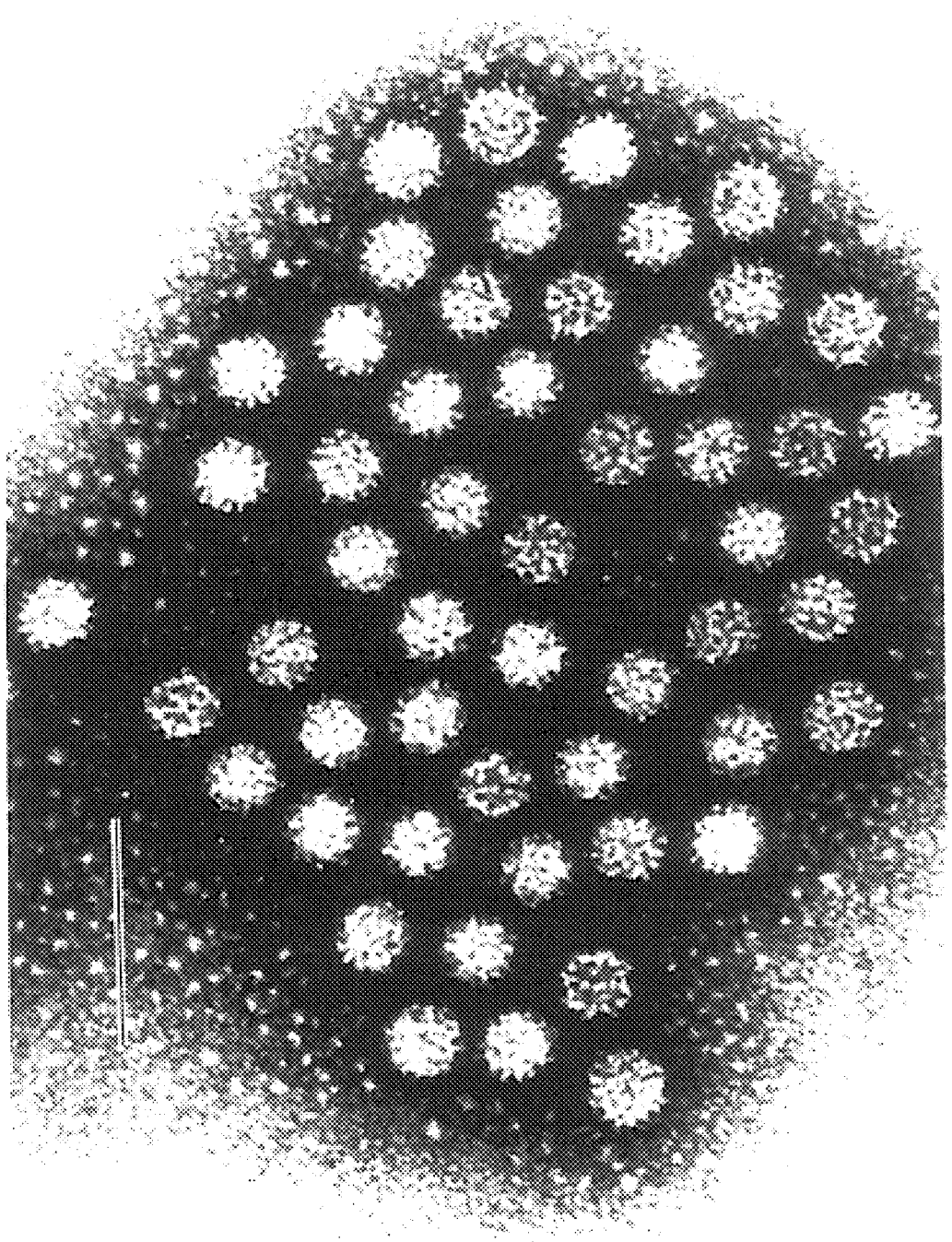

It is readily apparent to one skilled in the art that various substitutions and modifications may be made to the invention disclosed herein without departing from the scope and spirit of the invention.

The term "fragment" as used herein is defined as a fragment of a genome or a subgenomic clone that is required to be expressed to produce a peptide fragment which might be able to induce a polyclonal or monoclonal antibody. It is possible a peptide of only 5 amino acids could be immunogenic but usually peptides of 15 amino acids or longer are required. This depends on the properties of the peptide and it cannot be predicted in advance.

The term "derivative" as used herein is defined as larger pieces of DNA or an additional cDNA which represents the Norwalk genome and which is detected by direct or sequential use of the original cDNA and any deduced amino acid sequences thereof. Clone pUCNV-1011, therefore, is a derivative, although it does not overlap or share sequences with the original clone. Also included within the definition of derivative are RNA counterparts of DNA fragments and DNA or cDNA fragments in which one or more bases have been substituted or to which labels and end structures have been added without effecting the reading or expression of the DNA or cDNA.

Production of Norwalk Virus for Molecular Cloning

Norwalk virus was produced by administration of safety tested Norwalk virus (8FIIa) to adult volunteers. The virus inoculum used in the volunteer study, was kindly supplied by Dr. Albert Kapikian (Laboratory of Allergy and Infectious Diseases, National Institutes of Health, Bethesda, Md.). This virus originated from an outbreak of acute gastroenteritis in Norwalk, Ohio (Dolin et al., 1971). Two ml of a 1 to 100 dilution of 8FIIa in TBS was administered orally to each individual with 80 ml of milli-Q water (Millipore, Bedford, Mass. 01730). Sodium bicarbonate solution was taken by each person 2 min before and 5 min after virus administration. The volunteer studies were approved by the Institutional Review Board for Human Research at Baylor College of Medicine, at the Methodist Hospital and at the General Clinical Research Center. The virus was administered to the volunteers in the General Clinical Research Center where the volunteers were hospitalized and under extensive medical care for 4 days. All stools were collected and kept at −70° C. for later use.

Purification of Norwalk Viruses from Stool Samples

A 10% solution of stool samples in TBS was clarified by low speed centrifugation at 3000 rpm for 15 min. The resultant supernate were then extracted two to three times with genetron in the presence of 0.5% Zwittergent 3–14 detergent (Calbiochem Corp., La Jolla, Calif.). Viruses in the aqueous phase were concentrated by pelleting at 36,000 rpm for 90 minutes through a 40% sucrose cushion in a 50.2 Ti rotor (Beckman Instruments, Inc., Palo Alto, Calif. 94304). The pellets were suspended in TBS and mixed with CsCl solution (refractive index 1.368) and centrifuged at about 35,000 rpm for about 24 h in a SW50.1 rotor (Beckman). The CsCl gradient was fractionated by bottom puncture and each fraction was monitored for virus by EM examination. The peak fractions containing Norwalk virus were pooled and CsCl in the samples was diluted with TBS and removed by pelleting the viruses at about 35,000 rpm for 1 h. The purified virus was stored at about −70° C.

Extraction of Nucleic Acids from Purified Virus

One method of extraction involved treating purified Norwalk virus from CsCl gradients with proteinase K (400 ug/ml) in proteinase K buffer (0.1 M Tris—Cl pH 7.5, 12.5 mM EDTA, 0.15 M NaCl, 1% w/v SDS) at about 37° C. for about 30 min. The samples were then extracted once with phenol-chloroform and once with chloroform. Nucleic acids in the aqueous phase were concentrated by precipitation with 2.5 volumes of ethanol in the presence of 0.2 M NaOAc followed by pelleting for 15 min in a microcentrifuge.

cDNA Synthesis and Cloning of Amplified of cDNA

One method of synthesis and cloning included denaturing nucleic acids extracted from the purified Norwalk viruses with 10 mM $CH_3HgOH$. Then cDNA was synthesized using the cDNA synthesis kit with the supplied random hexanucleotide primer (Amersham, Arlington Heights, Ill. 60005). After the second strand synthesis, the reaction mixture was extracted once with phenol-chloroform and once with chloroform followed by ethanol precipitation. Amplification of DNA was performed using the random prime kit for DNA labeling (Promega Corp., Madison, Wis. 53711-5305). Eight cycles of denaturation (100° C. for 2 min), reannealing (2 min cooling to room temperature) and elongation (room temperature for 30 min) were performed after addition of Klenow fragment (Promega Corp.). A DNA library was constructed in pUC-13 with blunt-end ligation into the Sma I site.

Screening of the Library for Positive Clones

As one method of screening, white colonies from transformed DH5 alpha bacterial cells (BRL) were picked and both a master plate and minipreps of plasmid DNA were prepared for each clone. Clones containing inserts were identified after electrophoresis of the plasmid DNA in an agarose gel. The insert DNA in the agarose gel was cut out and labeled with $^{32}$P using random primers and Klenow DNA polymerase such as in the prime-a-gene® labeling system (Promega Corp.). Other isotopic or biochemical labels, such as enzymes, and fluorescent, chemiluminescent or bioluminescent substrates can also be used. Nucleic acids extracted from paired stool samples (before and after Norwalk infection) from two volunteers (543 and 544) were dotted onto Zetabind filters (AFM, Cuno, Meriden, Conn.). Replicate filter strips were prepared and hybridized with each labeled plasmid probe individually at 65° C. without formamide. Potential positive clones were judged by their different reactions with the pre- and post-infection stools. Clones which reacted with post- (but not pre-) infection stools of volunteers were considered positive and these clones on the master plates were characterized further. Once one Norwalk clone was identified, it was used to rescreen the cDNA library to identify additional overlapping clones. Rescreening the cDNA library with these additional clones can ultimately identify clones representing the entire Norwalk virus genome.

The following examples are offered by way of illustration and are not intended to limit the invention in any manner.

EXAMPLE 1

Electron Micrograph Confirmation

To permit better diagnosis and molecular characterization of Norwalk virus, a cDNA library was derived from nucleic acid extracted from virions purified from stool samples. Norwalk virus was purified with methods used previously for hepatitis A and rotaviruses from stool samples with some modifications (Jiang et al., 1986). Basically stool samples obtained from volunteers administered Norwalk virus were treated with Genetron to remove lipid and water insoluble materials. Virus in the aqueous phase was then pelleted through a 40% sucrose cushion. The resultant pellets were resuspended, sonicated and loaded in a CsCl gradient for isopycnic centrifugation. FIG. 1 shows an electron micrograph of purified Norwalk viruses after CsCl gradient centrifugation. Approximately $10^9$ physical particles were obtained from 500 grams of stools when the first cDNA library was made.

EXAMPLE 2

Initial cDNA Synthesis, Cloning and Screening

A cDNA library was generated from nucleic acids extracted from these purified viruses by proteinase K treatment of the samples followed by phenol-chloroform extraction and ethanol precipitation (Jiang et al., 1986; 1987). Because the nature of the viral genome was unknown, the extracted nucleic acids were denatured with methylmercuric hydroxide before cDNA synthesis. Random primed cDNA was synthesized with the Gubler-Hoffman method (cDNA synthesis system plus, Amersham) and a small amount of cDNA was obtained. Direct cloning of this small amount of cDNA was unsuccessful. Therefore, a step of amplification of the DNA was performed by synthesizing more copies of the DNA with random primers and the Klenow fragment of DNA polymerase before cloning. The procedure involved cycles of denaturation, addition of random primers and the Klenow fragment of DNA polymerase, reannealing and elongation. With this procedure, a linear incorporation of labeled nucleotides into product was observed as the number of cycles of synthesis was increased. The numbers of cycles performed were limited (<10) to avoid the synthesis of an excess of smaller fragments. In the case of Norwalk cDNA, 8 cycles of amplification were performed and approximately 2.5 ug of DNA were obtained, which was at least a 100-fold amplification of the starting template cDNA. This amplified cDNA was cloned into pUC-13 by blunt-end ligation and a positive clone (pUCNV-953) was isolated.

To obtain the positive Norwalk virus clone, minipreparations of the plasmid DNAs containing potential inserts were screened by agarose gel electrophoresis. Inserts of the larger clones in the gel were cut out and probes were made with the DNA in the gel using the prime-a-gene® labeling system (Promega Corp.). These probes were hybridized individually with paired stool samples (before and after Norwalk infection) from two volunteers (FIG. 2a). One clone (pUCNV-953) reacted with post- but not pre-infection stool samples from both volunteers.

EXAMPLE 3

Confirmation of Viral Origin of the Clone pUCNV-953

Figure 2B:
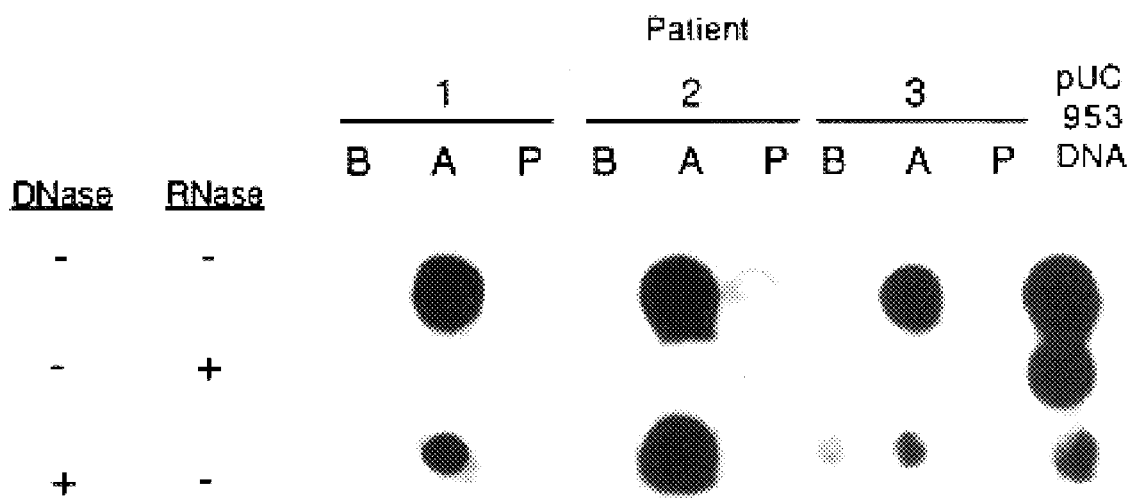
Figure 3:
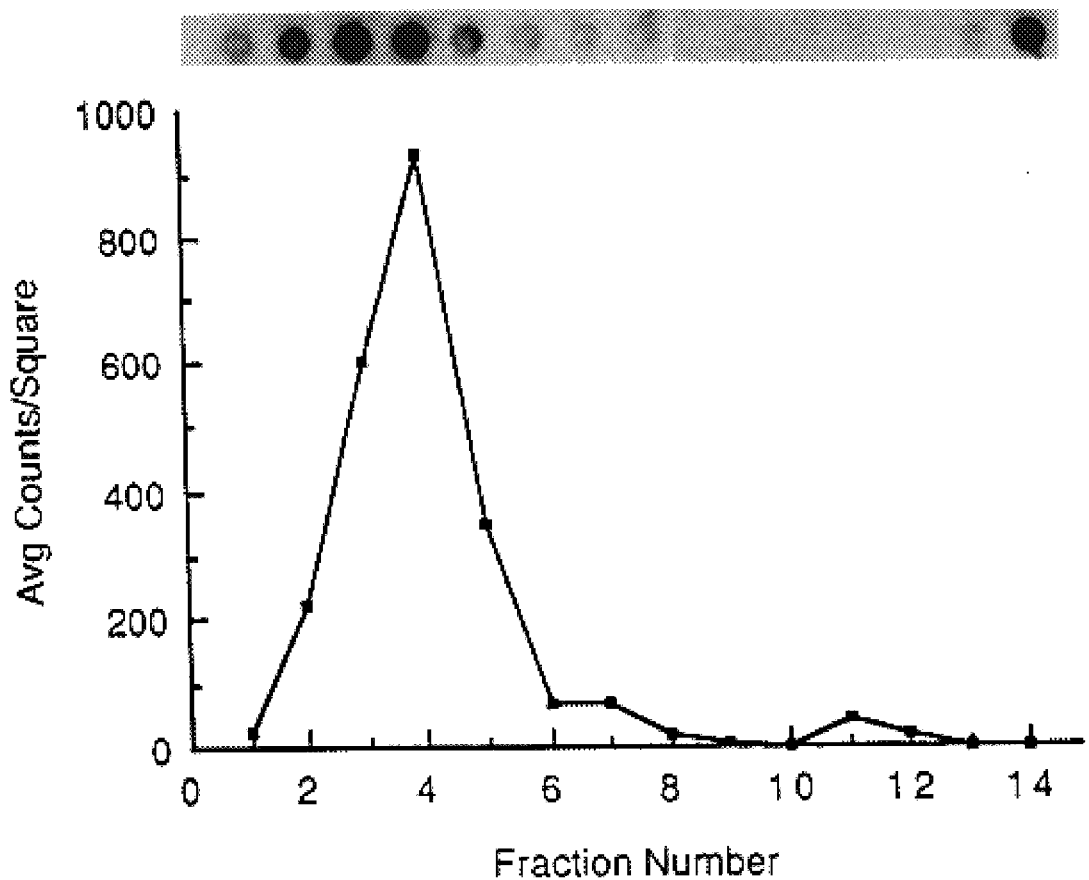
Figure 4:
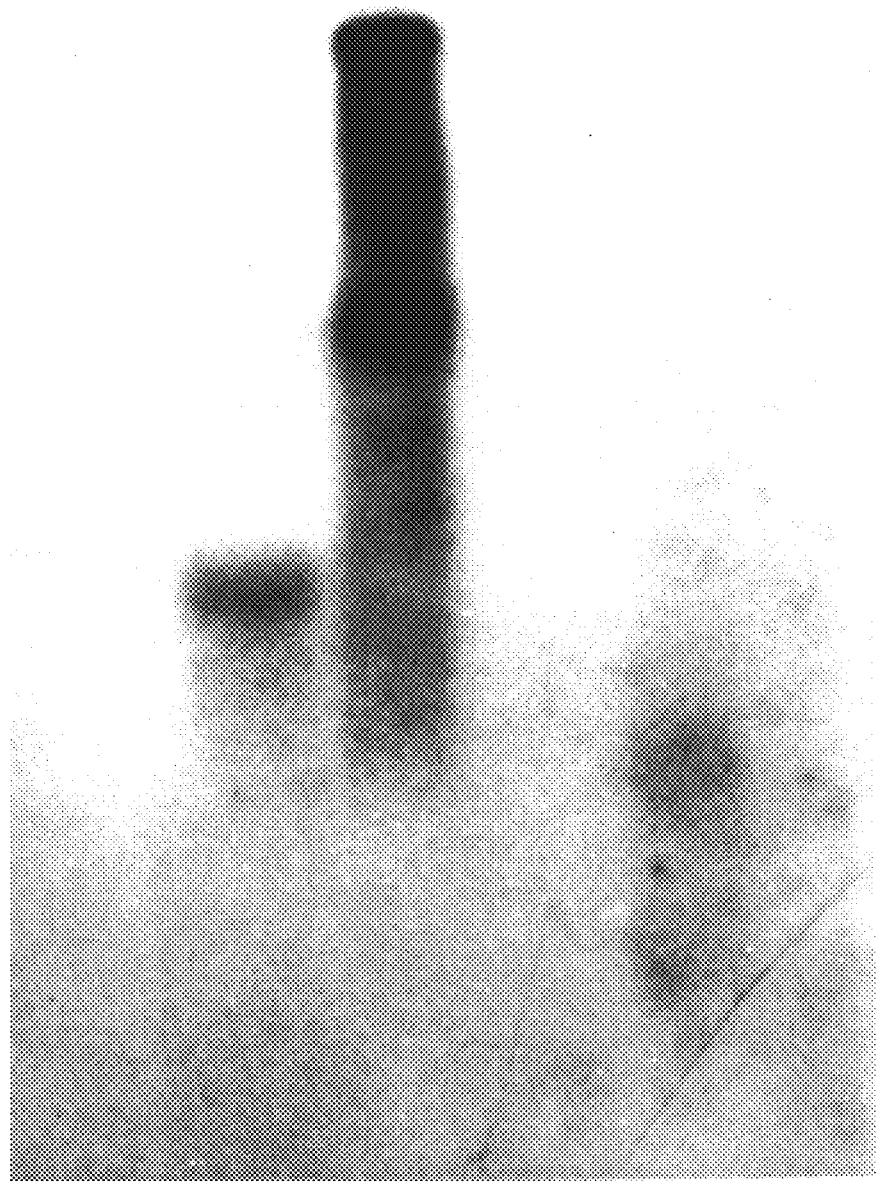
Figure 6:
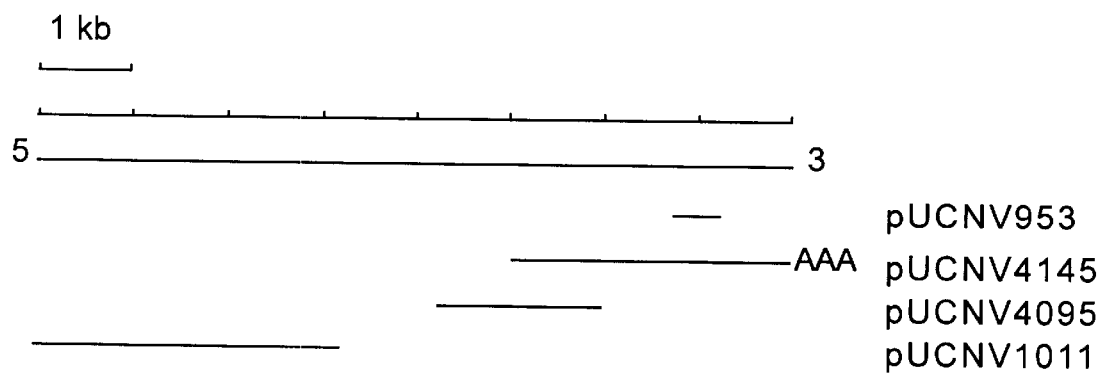

To further confirm the viral origin of the clone pUCNV-953, 6 more paired stool samples were tested and the same results were obtained. FIG. 2b shows a dot blot hybridization of the clone with stool samples collected at different times post-infection of the disease. Strong signals were observed only with stools from acute phase, but not before and after the illness. This result was consistent with previous RIA assays for viral antigen detection using convalescent sera from volunteers with Norwalk diarrhea and immune electron microscopy (IEM) studies of the samples for viral particle examination. This result also agrees with the patterns of virus shedding in stool in the course of the disease (Thornhill et al., 1975). When the clone was hybridized with fractions of a CsCl gradient from the Norwalk virus purification scheme, a correlation between hybridization and EM viral particle counts was observed (FIG. 3). The peaks of the hybridization signals and viral particle counts both were at fractions with a density of 1.38 g/cm$^3$, which agrees with previous reports of the biophysical properties of Norwalk virus. Finally, the clone was tested by hybridization with highly purified Norwalk virus electrophoresed on an agarose gel. A single hybridization band was observed with Norwalk virus but not with HAV (FIG. 4) and rotavirus (not shown). Sequence analysis of the pUCNV-953 cDNA showed this clone is 511 bp (FIG. 5). This partial genomic cDNA encodes a potential open reading frame for which the amino acid sequence has been deduced (FIG. 5). No significant nucleotide or deduced amino acid sequence homology was found by comparison with other sequences in the Gen Bank (Molecular Biology Information Resource, Eugene Software, Baylor College of Medicine).

EXAMPLE 4

Use of Norwalk Virus cDNA to Characterize the Viral Genome

The pUCNV-953 cDNA was subcloned into the transcription vector pGEM-3Zf(+) and grown. ssRNA probes were then generated by in vitro transcription using SP6 and T7 polymerases (Promega). When two opposite sense ssRNA probes were hybridized with the viral nucleic acid separately, only one strand reacted with the virus, indicating the viral genome is single-stranded. As shown in FIG. 2b, the hybridization signals were removed by treatment of the viral nucleic acid with RNAse (but not with DNAse) before loading them onto the filters, indicating the virus genome contains ssRNA. A long open reading frame was found in one of the two strands of the inserted DNA by the computer analysis of the sequences of pUCNV-953. The ssRNA probe with the same sequence as this coding strand does not react with the viral nucleic acid, but the complementary ssRNA probe does react in the hybridization tests. Therefore, Norwalk virus contains a positive sense single-stranded RNA genome. The size of the genome of Norwalk virus was estimated to be about 8 kb based on comparisons of the migration rate of the purified viral RNA in agarose gels with molecular weight markers. This size is slightly bigger than that of the picornaviruses [HAV and poliovirus; (FIG. 4)].

The pUCNV-953 cDNA used to rescreen a second cDNA library made as follows. A clone of the Norwalk or related virus was synthesized by isolating nucleic acid from purified Norwalk virus; cDNA was synthesized using reverse transcriptase and random primers; a second strand of DNA was synthesized from the cDNA; and at least one copy of DNA was inserted into a plasmid or a cloning and expression vector; and screening the library with the original puCNV-953 cDNA identified clones containing fragments of (or the complete) Norwalk or related genome. Alternatively at least one copy of DNA was inserted in a cloning and expression vector, such as lambda ZAPII® (Stratigene Inc.), and the cDNA library was screened to identify recombinant phage containing fragments of or the complete Norwalk or related genome. Additional cDNAs were made and found with this method. Use of these additional cDNAs to rescreen the library resulted in detection of new clones (FIG. 6). Use of the original pUCNV-953 and one additional non-overlapping cDNA (pUCNV-1011) as probes confirmed they detected virus (FIG. 7). Other overlapping cDNA (pUCNV-4145) and non-overlapping cDNA (pUCNV-4095) are useful probes to detect the Norwalk and related viruses.

Thus, the cDNA, or fragments or derivatives thereof, can be used in assays to detect the genome of Norwalk and other related viruses. The detection assays include labeled cDNA or ssRNA probes for direct detection of the Norwalk virus genome and measurement of the amount of probe binding. Alternatively, small oligonucleotide probes (10 nucleotides or greater) and polymerase chain reaction amplification are used to detect the Norwalk and related virus genomes. Expression of the open reading frame in the cDNA is used to make hyperimmune or monoclonal antibodies for use in diagnostic products and vaccines.

Using the above methodology, the following nucleotide sequence of the Norwalk virus genome has been identified.

```
GGCGTCAAAA GACGTCGTTC CTACTGCTGC TAGCAGTGAA   40

AATGCTAACA ACAATAGTAG TATTAAGTCT CGTCTATTGG   80

CGAGACTCAA GGGTTCAGGT GGGGCTACGT CCCCACCCAA  120

CTCGATAAAG ATAACCAACC AAGATATGGC TCTGGGGCTG  160

ATTGGACAGG TCCCAGCGCC AAAGGCCACA TCCGTCGATG  200
```

-continued

```
TCCCTAAACA ACAGAGGGAT AGACCACCAC GGACTGTTGC  240

CGAAGTTCAA CAAAATTTGC GTTGGACTGA GAGACCACAA  280

GACCAGAATG TTAAGACGTG GGATGAGCTT GACCACACAA  320

CAAAACAACA GATACTTGAT GAACACGCTG AGTGGTTTGA  360

TGCCGGTGGC TTAGGTCCAA GTACACTACC CACTAGTCAT  400

GAACGGTACA CACATGAGAA TGATGAAGGC CACCAGGTAA  440

AGTGGTCGGC TAGGGAAGGT GTAGACCTTG GCATATCCGG  480

GCTCACGACG GTGTCTGGGC CTGAGTGGAA TATGTGCCCG  520

CTACCACCAG TTGACCAAAG GAGCACGACA CCTGCAACTG  560

AGCCCACAAT TGGTGACATG ATCGAATTCT ATGAAGGGCA  600

CATCTATCAT TATGCTATAT ACATAGGTCA AGGCAAGACG  640

GTGGGTGTAC ACTCCCCTCA AGCAGCCTTC TCAATAACGA  680

GGATCACCAT ACAGCCCATA TCAGCTTGGT GGCGAGTCTG  720

TTATGTCCCA CAACCAAAAC AGAGGCTCAC ATACGACCAA  760

CTCAAAGAAT TAGAAAATGA ACCATGGCCG TATGCCGCAG  800

TCACGAACAA CTGCTTCGAA TTTTGTTGCC AGGTCATGTG  840

CTTGGAAGAT ACTTGGTTGC AAAGGAAGCT CATCTCCTCT  880

GGCCGGTTTT ACCACCCGAC CCAAGATTGG TCCCGAGACA  920

CTCCAGAATT CCAACAAGAC AGCAAGTTAG AGATGGTTAG  960

GGATGCAGTG CTAGCCGCTA TAAATGGGTT GGTGTCGCGG 1000

CCATTTAAAG ATCTTCTGGG TAAGCTCAAA CCCTTGAACG 1040

TGCTTAACTT ACTTTCAAAC TGTGATTGGA CGTTCATGGG 1080

GGTCGTGGAG ATGGTGGTCC TCCTTTTAGA ACTCTTTGGA 1120

ATCTTTTGGA ACCCACCTGA TGTTTCCAAC TTTATAGCTT 1160

CACTCCTGCC AGATTTCCAT CTACAGGGCC CCGAGGACCT 1200

TGCCAGGGAT CTCGTGCCAA TAGTATTGGG GGGGATCGGC 1240

TTAGCCATAG GATTCACCAG AGACAAGGTA AGTAAGATGA 1280

TGAAGAATGC TGTTGATGGA CTTCGTGCGG CAACCCAGCT 1320

CGGTCAATAT GGCCTAGAAA TATTCTCATT ACTAAAGAAG 1360

TACTTCTTCG GTGGTGATCA AACAGAGAAA ACCCTAAAAG 1400

ATATTGAGTC AGCAGTTATA GATATGGAAG TACTATCATC 1440

TACATCAGTG ACTCAGCTCG TGAGGGACAA ACAGTCTGCA 1480

CGGGCTTATA TGGCCATCTT AGATAATGAA GAAGAAAAGG 1520

CAAGGAAATT ATCTGTCAGG AATGCCGACC CACACGTAGT 1560

ATCCTCTACC AATGCTCTCA TATCCCGGAT CTCAATGGCT 1600

AGGGCTGCAT TGGCCAAGGC TCAAGCTGAA ATGACCAGCA 1640

GGATGCGTCC TGTGGTCATT ATGATGTGTG GGCCCCCTGG 1680

TATAGGTAAA ACCAAGGCAG CAGAACATCT GGCTAAACGC 1720

CTAGCCAATG AGATACGGCC TGGTGGTAAG GTTGGGCTGG 1760

TCCCACGGGA GGCAGTGGAT CATTGGGATG GATATCACGG 1800
```

-continued

```
AGAGGAAGTG ATGCTGTGGG ACGACTATGG AATGACAAAG   1840
ATACAGGAAG ACTGTAATAA ACTGCAAGCC ATAGCCGACT   1880
CAGCCCCCCT AACACTCAAT TGTGACCGAA TAGAAAACAA   1920
GGGAATGCAA TTTGTGTCTG ATGCTATAGT CATCACCACC   1960
AATGCTCCTG GCCCAGCCCC AGTGGACTTT GTCAACCTCG   2000
GGCCTGTTTG CCGAAGGGTG GACTTCCTTG TGTATTGCAC   2040
GGCACCTGAA GTTAACACA CGAGGAAAGT CAGTCCTGGG    2080
GACACAACTG CACTGAAAGA CTGCTTCAAG CCCGATTTCT   2120
CACATCTAAA AATGGAGTTG GCTCCCCAAG GGGGCTTTGA   2160
TAACCAAGGG AATACCCCGT TTGGTAAGGG TGTGATGAAG   2200
CCCACCACCA TAAACAGGCT GTTAATCCAG GCTGTAGCCT   2240
TGACGATGGA GAGACAGGAT GAGTTCCAAC TCCAGGGGCC   2280
TACGTATGAC TTTGATACTG ACAGAGTAGC TGCGTTCACG   2320
AGGATGGCCC GAGCCAACGG GTTGGGTCTC ATATCCATGG   2360
CCTCCCTAGG CAAAAAGCTA CGCAGTGTCA CCACTATTGA   2400
AGGATTAAAG AATGCTCTAT CAGGCTATAA AATATCAAAA   2440
TGCAGTATAC AATGGCAGTC AAGGGTGTAC ATTATAGAAT   2480
CAGATGGTGC CAGTGTACAA ATCAAAGAAG ACAAGCAAGC   2520
TTTGACCCCT CTGCAGCAGA CAATTAACAC GGCCTCACTT   2560
GCCATCACTC GACTCAAAGC AGCTAGGGCT GTGGCATACG   2600
CTTCATGTTT CCAGTCCGCC ATAACTACCA TACTACAAAT   2640
GGCGGGATCT GCGCTCGTTA TTAATCGAGC GGTCAAGCGT   2680
ATGTTTGGTA CCCGTACAGC AGCCATGGCA TTAGAAGGAC   2720
CTGGGAAAGA ACATAATTGC AGGGTCCATA AGGCTAAGGA   2760
AGCTGGAAAG GGGCCCATAG GTCATGATGA CATGGTAGAA   2800
AGGTTTGGCC TATGTGAAAC TGAAGAGGAG GAGAGTGAGG   2840
ACCAAATTCA AATGGTACCA AGTGATGCCG TCCCAGAAGG   2880
AAAGAACAAA GGCAAGACCA AAAAGGGACG TGGTCGCAAA   2920
AATAACTATA ATGCATTCTC TCGCCGTGGT CTGAGTGATG   2960
AAGAATATGA AGAGTACAAA AAGATCAGAG AAGAAAAGAA   3000
TGGCAATTAT AGTATACAAG AATACTTGGA GGACCGCCAA   3040
CGATATGAGG AAGAATTAGC AGAGGTACAG GCAGGTGGTG   3080
ATGGTGGCAT AGGAGAAACT GAAATGGAAA TCCGTCACAG   3120
GGTCTTCTAT AAATCCAAGA GTAAGAAACA CCAACAAGAG   3160
CAACGGCGAC AACTTGGTCT AGTGACTGGA TCAGACATCA   3200
GAAAACGTAA GCCCATTGAC TGGACCCCGC CAAAGAATGA   3240
ATGGGCAGAT GATGACAGAG AGGTGGATTA TAATGAAAAG   3280
ATCAATTTTG AAGCTCCCCC GACACTATGG AGCCGAGTCA   3320
CAAAGTTTGG ATCAGGATGG GGCTTTTGGG TCAGCCCGAC   3360
AGTGTTCATC ACAACCACAC ATGTAGTGCC AACTGGTGTG   3400
AAAGAATTCT TTGGTGAGCC CCTATCTAGT ATAGCAATCC   3440
ACCAAGCAGG TGAGTTCACA CAATTCAGGT TCTCAAAGAA   3480
AATGCGCCCT GACTTGACAG GTATGGTCCT TGAAGAAGGT   3520
TGCCCTGAAG GGACAGTCTG CTCAGTCCTA ATTAAACGGG   3560
ATTCGGGTGA ACTACTTCCG CTAGCCGTCC GTATGGGGGC   3600
TATTGCCTCC ATGAGGATAC AGGGTCGGCT TGTCCATGGC   3640
CAATCAGGGA TGTTACTGAC AGGGGCCAAT GCAAAGGGGA   3680
TGGATCTTGG CACTATACCA GGAGACTGCG GGGCACCATA   3720
CGTCCACAAG CGCGGGAATG ACTGGGTTGT GTGTGGAGTC   3760
CACGCTGCAG CCACAAAGTC AGGCAACACC GTGGTCTGCG   3800
CTGTACAGGC TGGAGAGGGC GAAACCGCAC TAGAAGGTGG   3840
AGACAAGGGG CATTATGCCG GCCACGAGAT TGTGAGGTAT   3880
GGAAGTGGCC CAGCACTGTC AACTAAAACA AAATTCTGGA   3920
GGTCCTCCCC AGAACCACTG CCCCCCGGAG TATATGAGCC   3960
AGCATACCTG GGGGGCAAGG ACCCCCGTGT ACAGAATGGC   4000
CCATCCCTAC AACAGGTACT ACGTGACCAA CTGAAACCCT   4040
TTGCGGACCC CCGCGGCCGC ATGCCTGAGC CTGGCCTACT   4080
GGAGGCTGCG GTTGAGACTG TAACATCCAT GTTAGAACAG   4120
ACAATGGATA CCCCAAGCCC GTGGTCTTAC GCTGATGCCT   4160
GCCAATCTCT TGACAAAACT ACTAGTTCGG GGTACCCTCA   4200
CCATAAAAGG AAGAATGATG ATTGGAATGG CACCACCTTC   4240
GTTGGAGAGC TCGGTGAGCA AGCTGCACAC GCCAACAATA   4280
TGTATGAGAA TGCTAAACAT ATGAAACCCA TTTACACTGC   4320
AGCCTTAAAA GATGAACTAG TCAAGCCAGA AAAGATTTAT   4360
CAAAAAGTCA AGAAGCGTCT ACTATGGGGC GCCGATCTCG   4400
GAACAGTGGT CAGGGCCGCC CGGGCTTTTG GCCCATTTTG   4440
TGACGCTATA AAATCACATG TCATCAAATT GCCAATAAAA   4480
GTTGGCATGA ACACAATAGA AGATGGCCCC CTCATCTATG   4520
CTGAGCATGC TAAATATAAG AATCATTTTG ATGCAGATTA   4560
TACAGCATGG GACTCAACAC AAAATAGACA AATTATGACA   4600
GAATCCTTCT CCATTATGTC GCGCCTTACG GCCTCACCAG   4640
AATTGGCCGA GGTTGTGGCC CAAGATTGC TAGCACCATC    4680
TGAGATGGAT GTAGGTGATT ATGTCATCAG GGTCAAAGAG   4720
GGGCTGCCAT CTGGATTCCC ATGTACTTCC CAGGTGAACA   4760
GCATAAATCA CTGGATAATT ACTCTCTGTG CACTGTCTGA   4800
GGCCACTGGT TTATCACCTG ATGTGGTGCA ATCCATGTCA   4840
TATTTCTCAT TTTATGGTGA TGATGAGATT GTGTCAACTG   4880
ACATAGATTT TGACCCAGCC CGCCTCACTC AAATTCTCAA   4920
GGAATATGGC CTCAAACCAA CAAGGCCTGA CAAAACAGAA   4960
GGACCAATAC AAGTGAGGAA AAATGTGGAT GGACTGGTCT   5000
```

```
                                                -continued
TCTTGCGGCG CACCATTTCC CGTGATGCGG CAGGGTTCCA  5040
AGGCAGGTTA GATAGGGCTT CGATTGAACG CCAAATCTTC  5080
TGGACCCGCG GGCCCAATCA TTCAGATCCA TCAGAGACTC  5120
TAGTGCCACA CACTCAAAGA AAAATACAGT TGATTTCACT  5160
TCTAGGGGAA GCTTCACTCC ATGGTGAGAA ATTTTACAGA  5200
AAGATTTCCA GCAAGGTCAT ACATGAAATC AAGACTGGTG  5240
GATTGGAAAT GTATGTCCCA GGATGGCAGG CCATGTTCCG  5280
CTGGATGCGC TTCCATGACC TCGGATTGTG GACAGGAGAT  5320
CGCGATCTTC TGCCCGAATT CGTAAATGAT GATGCGTCTA  5360
                                        **
AGGACGCTAC ATCAAGCGTG GATGGCGCTA GTGGCGCTGG  5400
TCAGTTGGTA CCGGAGGTTA ATGCTTCTGA CCCTCTTGCA  5440
ATGGATCCTG TAGCAGGTTC TTCGACAGCA GTCGCGACTG  5480
CTGGACAAGT TAATCCTATT GATCCCTGGA TAATTAATAA  5520
TTTTGTGCAA GCCCCCCAAG GTGAATTTAC TATTTCCCCA  5560
AATAATACCC CCGGTGATGT TTTGTTTGAT TTGAGTTTGG  5600
GTCCCCATCT TAATCCTTTC TTGCTCCATC TATCACAAAT  5640
GTATAATGGT TGGGTTGGTA ACATGAGAGT CAGGATTATG  5680
CTAGCTGGTA ATGCCTTTAC TGCGGGGAAG ATAATAGTTT  5720
CCTGCATACC CCCTGGTTTT GGTTCACATA ATCTTACTAT  5760
AGCACAAGCA ACTCTCTTTC CACATGTGAT TGCTGATGTT  5800
AGGACTCTAG ACCCCATTGA GGTGCCTTTG GAAGATGTTA  5840
GGAATGTTCT CTTTCATAAT AATGATAGAA ATCAACAAAC  5880
CATGCGCCTT GTGTGCATGC TGTACACCCC CCTCCGCACT  5920
GGTGGTGGTA CTGGTGATTC TTTTGTAGTT GCAGGGCGAG  5960
TTATGACTTG CCCCAGTCCT GATTTTAATT TCTTGTTTTT  6000
AGTCCTCCT ACGGTGGAGC AGAAAACCAG GCCCTTCACA  6040
CTCCCAAATC TGCCATTGAG TTCTCTGTCT AACTCACGTG  6080
CCCCTCTCCC AATCAGTAGT ATGGGCATTT CCCCAGACAA  6120
TGTCCAGAGT GTGCAGTTCC AAAATGGTCG GTGTACTCTG  6160
GATGCCGCC TGGTTGGCAC CACCCAGTT TCATTGTCAC  6200
ATGTTGCCAA GATAAGAGGG ACCTCCAATG GCACTGTAAT  6240
CAACCTTACT GAATTGGATG GCACACCCTT TCACCCTTTT  6280
GAGGGCCCTG CCCCCATTGG GTTTCCAGAC CTCGGTGGTT  6320
GTGATTGGCA TATCAATATG ACACAGTTTG GCCATTCTAG  6360
CCAGACCCAG TATGATGTAG ACACCACCCC TGACACTTTT  6400
GTCCCCCATC TTGGTTCAAT TCAGGCAAAT GGCATTGGCA  6440
GTGGTAATTA TGTTGGTGTT CTTAGCTGGA TTTCCCCCCC  6480
ATCACACCCG TCTGGCTCCC AAGTTGACCT TGGAAGATC   6520
CCCAATTATG GGTCAAGTAT TACGGAGGCA ACACATCTAG  6560
CCCCTTCTGT ATACCCCCCT GGTTTCGGAG AGGTATTGGT  6600

-continued
CTTTTTCATG TCAAAAATGC CAGGTCCTGG TGCTTATAAT  6640
TTGCCCTGTC TATTACCACA AGAGTACATT TCACATCTTG  6680
CTAGTGAACA AGCCCCTACT GTAGGTGAGG CTGCCCTGCT  6720
CCACTATGTT GACCCTGATA CCGGTCGGAA TCTTGGGGAA  6760
TTCAAAGCAT ACCCTGATGG TTTCCTCACT TGTGTCCCCA  6800
ATGGGGCTAG CTCGGGTCCA CAACAGCTGC CGATCAATGG  6840
GGTCTTTGTC TTTGTTTCAT GGGTGTCCAG ATTTTATCAA  6880
TTAAAGCCTG TGGGAACTGC CAGCTCGGCA AGAGGTAGGC  6920
TTGGTCTGCG CCGATAATGG CCCAAGCCAT AATTGGTGCA  6960
ATTGCTGCTT CCACAGCAGG TAGTGCTCTG GGAGCGGGCA  7000
TACAGGTTGG TGGCGACAGG CCCTCCAAAG CCAAAGGTAT  7040
CAACAAAATT TGCAACTGCA AGAAAATTCT TTTAAACATG  7080
ACAGGGAAAT GATTGGGTAT CAGGTTGAAG CTTCAAATCA  7120
ATTATTGGCT AAAAATTTGG CAACTAGATA TTCACTCCTC  7160
CGTGCTGGGG GTTTGACCAG TGCTGATGCA GCAAGATCTG  7200
TGGCAGGAGC TCCAGTCACC CGCATTGTAG ATTGGAATGG  7240
CGTGAGAGTG TCTGCTCCCG AGTCCTCTGC TACCACATTG  7280
AGATCCGGTG GCTTCATGTG AGTTCCCATA CCATTTGCCT  7320
CTAAGCAAAA ACAGGTTCAA TCATCTGGTA TTAGTAATCC  7360
AAATTATTCC CCTTCATCCA TTTCTCGAAC CACTAGTTGG  7400
GTCGAGTCAC AAAACTCATC GAGATTTGGA AATCTTTCTC  7440
CATACCACGC GGAGGCTCTC AATACAGTGT GGTTGACTCC  7480
ACCCGGTTCA ACAGCCTCTT CTACACTGTC TTCTGTGCCA  7520
CGTGGTTATT TCAATACAGA CAGGTTGCCA TTATTCGCAA  7560
ATAATAGGCG ATGATGTTGT AATATGAAAT GTGGGCATCA  7600
TATTCATTTA ATTAGGTTTA ATTAGGTTTA ATTTGATGTT  7640
AAAAAAAAAA AAAAAAAAAA AAAAAAAAAA AAAAAAAAAA  7680
AAAAAAAAAA AAAAAAAAAA AAAAAAAAAA AAAAAAAAAA  7720
AA                                          7722
```

Within the sequence, there may be an additional base of G between G and C at nucleotides 5354 and 5355. The above cDNA sequence is referred to as Norwalk virus cDNA or SEQ. ID. NO. 1.

Also, within the above nucleotide sequence at base 4543 to 4924 is an RNA-dependent RNA polymerase.

```
CAT TTT GAT GCA GAT TAT ACA GCA TGG GAC TCA ACA CAA AAT
HIS PHE ASP ALA ASP TYR THR ALA TRP ASP SER THR GLN ASN
            5                   10

AGA CAA ATT ATG ACA GAA TCC TTC TCC ATT ATG TCG CGC CTT
ARG GLN ILE MET THR GLU SER PHE SER THR MET SER ARG LEU
15                  20                  25

ACG GCC TCA CCA GAA TTG GCC GAG GTT GTG GCC CAA GAT TTG
THR ALA SER PRO GLU LEU ALA GLU VAL VAL ALA GLN ASP LEU
        30                  35                  40

CTA GCA CCA TCT GAG ATG GAT GTA GGT GAT TAT GTC ATC AGG
LEU ALA PRO SER GLU MET ASP VAL GLY ASP TYR VAL ILE ARG
            50                  55                  60

GTC AAA GAG GGG CTG CCA TCT GGA TTC CCA TGT ACT TCC CAG
VAL LYS GLU GLY LEU PRO SER GLY PHE PRO CYS THR SER GLN
                65                  70                  75

GTG AAC AGC ATA AAT CAC TGG ATA ATT ACT CTC TGT GCA CTG
VAL ASN SER ILE ASN HIS TRP ILE ILE THR LEU CYS ALA LEU
                    80                  85

TCT GAG GCC ACT GGT TTA TCA CCT GAT GTG GTG CAA TCC ATG
SER GLU ALA THR GLY LEU SER PRO ASP VAL VAL GLN SER MET
90                      95                  100

TCA TAT TTC TCA TTT TAT GGT GAT GAT GAG ATT GTG TCA ACT
SER TYR PHE SER PHE TYR GLY ASP ASP GLU ILE VAL SER THR
    105                     110                 115

GAC ATA GAT TTT GAC CCA GCC CGC CTC ACT CAA ATT CTC AAG GAA
ASP ILE ASP PHE ASP PRO ALA ARG LEU THR GLN ILE LEU LYS GLU
        120                 125                 130
```

The fact that this portion of the genome is a RNA polymerase is verified by comparisons with RNA polymerase in other positive sense RNA viruses (FIG. 8).

EXAMPLE 5

Diagnostic Assays Based on Detection of the Sequences of the Norwalk Virus Genome Hybridization assays are the assays of choice to detect Norwalk virus because small amounts of virus are present in clinical or contaminated water and food specimens. Previously, the possibility to detect Norwalk and related nucleic acids was not possible because the genome of Norwalk virus was not known and no sequence information was available. Probes made from the Norwalk virus cDNA or primers made from the Norwalk virus genome sequence allow methods to amplify the genome for diagnostic products to be established. Probes to identify Norwalk virus alone and to identify other viruses in the Norwalk group enable development of either specific assays for Norwalk or general assays to detect sequences common to many or all of these agents.

In the past, one major difficulty encountered in RT-PCR detection of viral RNA in stool samples was that uncharacterized factor(s) are present in stools which inhibit the enzymatic activity of both reverse transcriptase and Taq polymerase (Wilde et al., J Clin Microbiol 28:1300–1307, 1990). These factor(s) were difficult to remove by routine methods of nucleic acid extraction. Techniques were developed using cetyltrimethylammonium bromide (CTAB) and oligo d(T) cellulose to specifically separate viral RNA from the inhibitory factor(s). These techniques were based on the unique properties of CTAB which selectively precipitates nucleic acid while leaving acid insoluble polysaccharide in the supernatant. The resulting nucleic acid was further purified by adsorption onto and elution from oligo d(T) cellulose. This step removes unrelated nucleic acids that lack a poly(A) tail. With this technique, Norwalk virus was detected easily by PCR in very small amounts (400 ul of a 10% suspension) of stool sample. For example, one skilled in the art will recognize that it is now possible to clone the genome of RNA viruses present in low concentrations in small amounts of stool after RT-PCR and a step of amplification of the viral RNA by RT-PCR using random primers. In addition, now that the inhibitor(s) can be removed from stool, it will also be possible to detect and clone nucleic acids of other viruses (DNA viruses, non-poly(A) tailed RNA viruses) present in stool.

The CTAB and oligo d(T) cellulose technique of extraction followed by detection of viral RNA with RT-PCR was used on stool samples and could be used on water and food samples. Stool sample was suspended in distilled water (about 10% wt/vol) and extracted once with genetron. Viruses in the supernatant were precipitated with polyehtylene glycol at a final concentration of about 8%. The viral pellets were treated with proteinase K (About 400 ug/ml) in the presence of SDS at about 37° C. for about 30 min. followed by one extraction with phenol chloroform and one with chloroform. A solution of about 5% CTAB and about 0.4M NaCl was added at a ratio of sample:CTAB=about 5:2. After incubation at about room temperature for about 15 min and at about 45° C. for about 5 min, the nucleic acids (including the viral RNA) were collected by centrifugation in a microcentrifuge for about 30 min. The resultant pellets were suspended in about 1M NaCl and extracted twice with chloroform. The viral RNA in the aqueous phase was used directly in RT-PCR reactions or further purified by adsorption/elution on oligo d(T) cellulose.

A batch method of adsorption/elution on oligo d(T) cellulose was used to purify poly(A) tailed RNA. In this procedure, nucleic acids partially purified as described above or RNA extracted directly with phenol chloroform (without CTAB treatment) were mixed with oligo d(T) cellulose (about 2–4 mg/sample) in a binding buffer (about 0.5M NaCl and 10 mM Tris, pH 7.5). The mixture was incubated at about 4° C. for about 1 hr with gentle shaking and then centrifuged for about 2 min in a microcentrifuge. The oligo d(T) cellulose pellet was washed 3–4 times with binding buffer and then the poly(A) tailed RNA was eluted with 1X TE buffer (about 10 mM Tris, 1 mM EDTA, pH 7.5). The supernate was collected following centrifugation to remove the oligo d(T) cellulose and the viral RNA in the supernate was precipitated with ethanol. The RNA obtained at this stage was basically inhibitor-free and able to be used in RT-PCR.

In preliminary experiments, Norwalk virus RNA was detected in less than 0.05 g of stool samples using the CTAB technique. A trace inhibitor activity was observed with RNA extracted with either CTAB or oligo d(T) alone, but this was easily removed by dilution (1:2) of the extracted nucleic acid before RT-PCR. Combination of the CTAB and oligo d(T) techniques resulted in obtaining high quality, inhibitor free RNA which could be used directly for RT-PCR detection and for cloning of the viral genome. With development of this method to clone from small amounts of stool, one skilled in the art will know that we will now be able to obtain cDNAs for the remainder of the genome including those representing the 5'-end of the genome.

Figure 9:
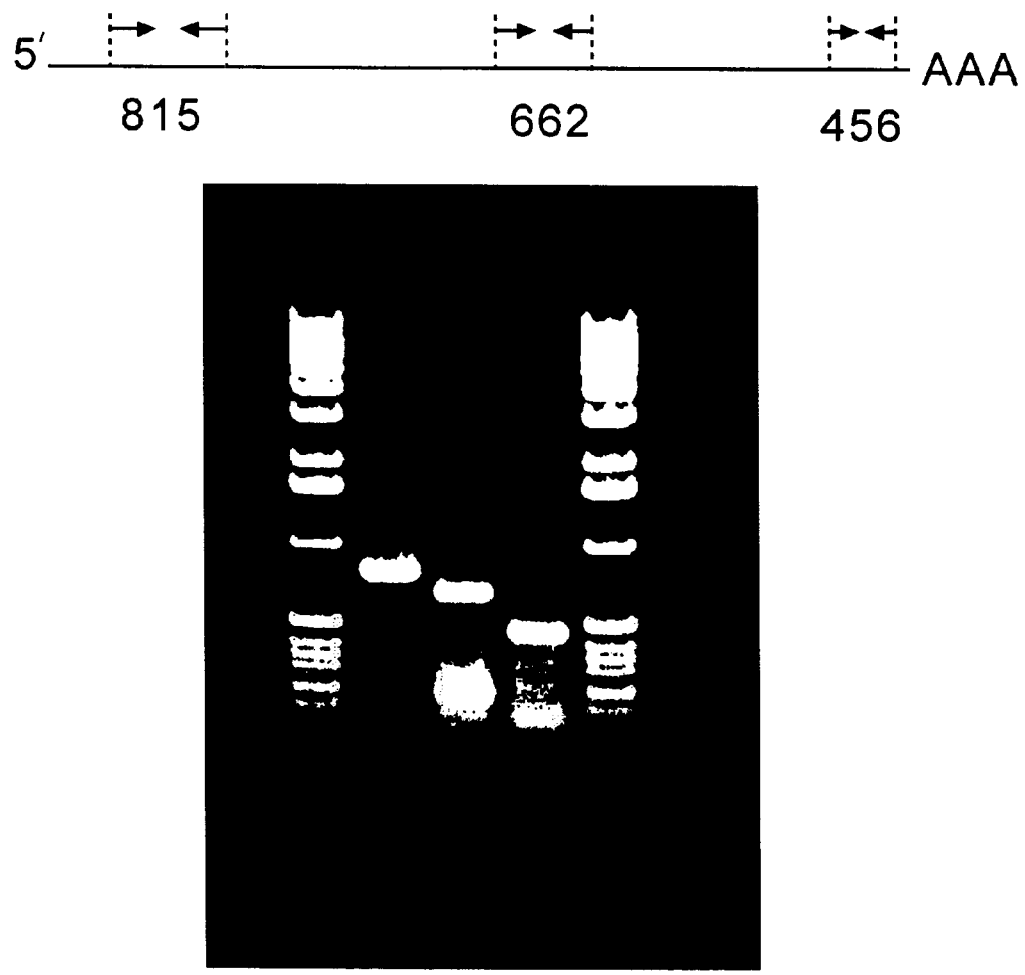

For detection with PCR, primers based on the above nucleotide sequence of the genome were made. These primers include: Primer 1: CACGCGGAGGCTCTCAAT located at nucleotides 7446 to 7463; Primer 4: GGTGGCGACAG-GCCCTCC located at nucleotides 7009 to 7026; Primer 8: TCAGCAGTTATAGATATG located at nucleotides 1409 to 1426; Primer 9: ATGCTATATACATAGGTC located at nucleotides 612 to 629; Primer 16: CAACAGGTAC-TACGTGAC located at nucleotides 4010 to 4027; and Primer 17: TGTGGCCCAAGATTTGCT located at nucleotides 4654 to 4671. These primers have been shown to be useful to detect virus using reverse transcription and polymerase chain reaction methods (RT-PCR). FIG. 9 shows data using these primers.

EXAMPLE 6

Preparation of Polyclonal Antibodies and Monoclonal Antibodies to Norwalk Virus Proteins Protein(s) encoded in the cDNA fragments or derivatives thereof, is produced in a prokaryotic or eukaryotic expression system and used to immunize animals to produce polyclonal antibodies for diagnostic assays. Prokaryotic hosts may include Gram negative as well as Gram positive bacteria, such as *E. coli, S. tymphimurium, Serratia marcescens,* and *Bacillus subtilis.* Eukaryotic hosts may include yeasts such as *Pichia pastoris* or insect or mammalian cells. Immunized animals may include mammals such as guinea pigs, mice, rabbits, cows, goats or horses or other non-mammalian or non-murine species such as chickens. Repeated immunization of these animals with the expressed protein mixed with an adjuvant such as Freund adjuvant to enhance stimulation of an immune response produces antibodies to the protein.

Alternatively, synthetic peptides of greater than 15 amino acids made to match the amino acid sequence deduced from the partial cDNA sequence (or from other sequences determined by sequencing additional cDNAs detected with the original or other clones) are linked to a carrier protein such as bovine serum albumin or lysozyme or cross-linked with treatment with gluteraldehyde and used to immunize animals to produce polyclonal antibodies for diagnostic tests.

The serum of animals immunized with either the expressed protein or with synthetic peptides are tested by immunologic assays such as immune electron microscopy, Western blots (immunoblots) and blocking ELISAs to demonstrate that antibodies to Norwalk and related viruses have been made. Reactivities with the expressed protein or synthetic peptides show specificity of the polyclonal sera. Reactivities with other viruses in the Norwalk group (Snow Mountain Agent, Hawaii Agent, Taunton Agent, etc.) indicate production of a reagent which recognizes cross-reacting epitopes.

Balb\c mice injected with the immunogens as described above and shown to have produced polyclonal antibodies are boosted with immunogen and then sacrificed. Their spleens are removed for fusion of splenocytes with myeloma cells to produce hybridomas. Hybridomas resulting from this fusion are screened for their reactivity with the expressed protein, the peptide and virus particles to select cells producing monoclonal antibodies to Norwalk virus. Screening of such hybridomas with Norwalk-related viruses permits identification of hybridomas secreting monoclonal antibodies to these viruses as well.

The novel features characteristic of this invention are set forth in the appended claims. The present invention is well adapted to carry out the objects and obtain the ends and advantages mentioned, as well as others inherent therein. While presently preferred embodiments of the invention have been described for the purpose of disclosure, numerous changes in the details of synthesis and use described herein will be apparent to those skilled in the art. It should be understood, however, that there is no intention to limit the invention to the specific form disclosed, but on the contrary, the intention is to cover all modifications, alternative means of synthesis and use and equivalents falling within the spirit and scope of the invention.

What is claimed is:

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
(A) LENGTH: 7722 base pairs
(B) TYPE: nucleic acid
(C) STRANDEDNESS: single
(D) TOPOLOGY: unknown (ii) MOLECULE TYPE: cDNA (vi) ORIGINAL SOURCE:
(A) ORGANISM: Norwalk virus
(B) STRAIN: 8FIIa
(C) INDIVIDUAL ISOLATE: 8FIIa (vii) IMMEDIATE SOURCE:
(B) CLONE: pUCNV-953 and its derivatives (xi) SEQUENCE DESCRIPTION: SEQ ID NO:1:

```
GGCGTCAAAA GACGTCGTTC CTACTGCTGC TAGCAGTGAA AATGCTAACA ACAATAGTAG     60

TATTAAGTCT CGTCTATTGG CGAGACTCAA GGGTTCAGGT GGGGCTACGT CCCCACCCAA    120

CTCGATAAAG ATAACCAACC AAGATATGGC TCTGGGGCTG ATTGGACAGG TCCCAGCGCC    180

AAAGGCCACA TCCGTCGATG TCCCTAAACA ACAGAGGGAT AGACCACCAC GGACTGTTGC    240

CGAAGTTCAA CAAAATTTGC GTTGGACTGA GAGACCACAA GACCAGAATG TTAAGACGTG    300

GGATGAGCTT GACCACACAA CAAAACAACA GATACTTGAT GAACACGCTG AGTGGTTTGA    360

TGCCGGTGGC TTAGGTCCAA GTACACTACC CACTAGTCAT GAACGGTACA CACATGAGAA    420

TGATGAAGGC CACCAGGTAA AGTGGTCGGC TAGGGAAGGT GTAGACCTTG GCATATCCGG    480

GCTCACGACG GTGTCTGGGC CTGAGTGGAA TATGTGCCCG CTACCACCAG TTGACCAAAG    540

GAGCACGACA CCTGCAACTG AGCCCACAAT TGGTGACATG ATCGAATTCT ATGAAGGGCA    600

CATCTATCAT TATGCTATAT ACATAGGTCA AGGCAAGACG GTGGGTGTAC ACTCCCCTCA    660

AGCAGCCTTC TCAATAACGA GGATCACCAT ACAGCCCATA TCAGCTTGGT GGCGAGTCTG    720

TTATGTCCCA CAACCAAAAC AGAGGCTCAC ATACGACCAA CTCAAAGAAT TAGAAAATGA    780

ACCATGGCCG TATGCCGCAG TCACGAACAA CTGCTTCGAA TTTTGTTGCC AGGTCATGTG    840

CTTGGAAGAT ACTTGGTTGC AAAGGAAGCT CATCTCCTCT GGCCGGTTTT ACCACCCGAC    900

CCAAGATTGG TCCCGAGACA CTCCAGAATT CCAACAAGAC AGCAAGTTAG AGATGGTTAG    960

GGATGCAGTG CTAGCCGCTA TAAATGGGTT GGTGTCGCGG CCATTTAAAG ATCTTCTGGG   1020

TAAGCTCAAA CCCTTGAACG TGCTTAACTT ACTTTCAAAC TGTGATTGGA CGTTCATGGG   1080

GGTCGTGGAG ATGGTGGTCC TCCTTTTAGA ACTCTTTGGA ATCTTTTGGA ACCCACCTGA   1140

TGTTTCCAAC TTTATAGCTT CACTCCTGCC AGATTTCCAT CTACAGGGCC CCGAGGACCT   1200

TGCCAGGGAT CTCGTGCCAA TAGTATTGGG GGGGATCGGC TTAGCCATAG GATTCACCAG   1260

AGACAAGGTA AGTAAGATGA TGAAGAATGC TGTTGATGGA CTTCGTGCGG CAACCCAGCT   1320

CGGTCAATAT GGCCTAGAAA TATTCTCATT ACTAAAGAAG TACTTCTTCG GTGGTGATCA   1380

AACAGAGAAA ACCCTAAAAG ATATTGAGTC AGCAGTTATA GATATGGAAG TACTATCATC   1440

TACATCAGTG ACTCAGCTCG TGAGGGACAA ACAGTCTGCA CGGGCTTATA TGGCCATCTT   1500
```

```
AGATAATGAA GAAGAAAAGG CAAGGAAATT ATCTGTCAGG AATGCCGACC CACACGTAGT      1560

ATCCTCTACC AATGCTCTCA TATCCCGGAT CTCAATGGCT AGGGCTGCAT TGGCCAAGGC      1620

TCAAGCTGAA ATGACCAGCA GGATGCGTCC TGTGGTCATT ATGATGTGTG GGCCCCCTGG      1680

TATAGGTAAA ACCAAGGCAG CAGAACATCT GGCTAAACGC CTAGCCAATG AGATACGGCC      1740

TGGTGGTAAG GTTGGGCTGG TCCCACGGGA GGCAGTGGAT CATTGGGATG GATATCACGG      1800

AGAGGAAGTG ATGCTGTGGG ACGACTATGG AATGACAAAG ATACAGGAAG ACTGTAATAA      1860

ACTGCAAGCC ATAGCCGACT CAGCCCCCCT AACACTCAAT TGTGACCGAA TAGAAAACAA      1920

GGGAATGCAA TTTGTGTCTG ATGCTATAGT CATCACCACC AATGCTCCTG GCCCAGCCCC      1980

AGTGGACTTT GTCAACCTCG GGCCTGTTTG CCGAAGGGTG GACTTCCTTG TGTATTGCAC      2040

GGCACCTGAA GTTGAACACA CGAGGAAAGT CAGTCCTGGG GACACAACTG CACTGAAAGA      2100

CTGCTTCAAG CCCGATTTCT CACATCTAAA AATGGAGTTG GCTCCCCAAG GGGCTTTGA      2160

TAACCAAGGG AATACCCCGT TTGGTAAGGG TGTGATGAAG CCCACCACCA TAAACAGGCT      2220

GTTAATCCAG GCTGTAGCCT TGACGATGGA GAGACAGGAT GAGTTCCAAC TCCAGGGGCC      2280

TACGTATGAC TTTGATACTG ACAGAGTAGC TGCGTTCACG AGGATGGCCC GAGCCAACGG      2340

GTTGGGTCTC ATATCCATGG CCTCCCTAGG CAAAAAGCTA CGCAGTGTCA CCACTATTGA      2400

AGGATTAAAG AATGCTCTAT CAGGCTATAA AATATCAAAA TGCAGTATAC AATGGCAGTC      2460

AAGGGTGTAC ATTATAGAAT CAGATGGTGC CAGTGTACAA ATCAAAGAAG ACAAGCAAGC      2520

TTTGACCCCT CTGCAGCAGA CAATTAACAC GGCCTCACTT GCCATCACTC GACTCAAAGC      2580

AGCTAGGGCT GTGGCATACG CTTCATGTTT CCAGTCCGCC ATAACTACCA TACTACAAAT      2640

GGCGGGATCT GCGCTCGTTA TTAATCGAGC GGTCAAGCGT ATGTTTGGTA CCCGTACAGC      2700

AGCCATGGCA TTAGAAGGAC CTGGGAAAGA ACATAATTGC AGGGTCCATA AGGCTAAGGA      2760

AGCTGGAAAG GGGCCCATAG GTCATGATGA CATGGTAGAA AGGTTTGGCC TATGTGAAAC      2820

TGAAGAGGAG GAGAGTGAGG ACCAAATTCA AATGGTACCA AGTGATGCCG TCCCAGAAGG      2880

AAAGAACAAA GGCAAGACCA AAAAGGGACG TGGTCGCAAA AATAACTATA ATGCATTCTC      2940

TCGCCGTGGT CTGAGTGATG AAGAATATGA AGAGTACAAA AAGATCAGAG AAGAAAAGAA      3000

TGGCAATTAT AGTATACAAG AATACTTGGA GGACCGCCAA CGATATGAGG AAGAATTAGC      3060

AGAGGTACAG GCAGGTGGTG ATGGTGGCAT AGGAGAAACT GAAATGGAAA TCCGTCACAG      3120

GGTCTTCTAT AAATCCAAGA GTAAGAAACA CCAACAAGAG CAACGGCGAC AACTTGGTCT      3180

AGTGACTGGA TCAGACATCA GAAAACGTAA GCCCATTGAC TGGACCCCGC AAAGAATGA      3240

ATGGGCAGAT GATGACAGAG AGGTGGATTA TAATGAAAAG ATCAATTTTG AAGCTCCCCC      3300

GACACTATGG AGCCGAGTCA CAAAGTTTGG ATCAGGATGG GGCTTTTGGG TCAGCCCGAC      3360

AGTGTTCATC ACAACCACAC ATGTAGTGCC AACTGGTGTG AAAGAATTCT TTGGTGAGCC      3420

CCTATCTAGT ATAGCAATCC ACCAAGCAGG TGAGTTCACA CAATTCAGGT TCTCAAAGAA      3480

AATGCGCCCT GACTTGACAG GTATGGTCCT TGAAGAAGGT TGCCCTGAAG GACAGTCTG      3540

CTCAGTCCTA ATTAAACGGG ATTCGGGTGA ACTACTTCCG CTAGCCGTCC GTATGGGGGC      3600

TATTGCCTCC ATGAGGATAC AGGGTCGGCT TGTCCATGGC CAATCAGGGA TGTTACTGAC      3660

AGGGGCCAAT GCAAAGGGGA TGGATCTTGG CACTATACCA GGAGACTGCG GGGCACCATA      3720

CGTCCACAAG CGCGGGAATG ACTGGGTTGT GTGTGGAGTC CACGCTGCAG CCACAAAGTC      3780

AGGCAACACC GTGGTCTGCG CTGTACAGGC TGGAGAGGGC GAAACCGCAC TAGAAGGTGG      3840
```

```
AGACAAGGGG CATTATGCCG GCCACGAGAT TGTGAGGTAT GGAAGTGGCC CAGCACTGTC      3900

AACTAAAACA AAATTCTGGA GGTCCTCCCC AGAACCACTG CCCCCCGGAG TATATGAGCC      3960

AGCATACCTG GGGGGCAAGG ACCCCCGTGT ACAGAATGGC CCATCCCTAC AACAGGTACT      4020

ACGTGACCAA CTGAAACCCT TTGCGGACCC CCGCGGCCGC ATGCCTGAGC CTGGCCTACT      4080

GGAGGCTGCG GTTGAGACTG TAACATCCAT GTTAGAACAG ACAATGGATA CCCCAAGCCC      4140

GTGGTCTTAC GCTGATGCCT GCCAATCTCT TGACAAAACT ACTAGTTCGG GGTACCCTCA      4200

CCATAAAAGG AAGAATGATG ATTGGAATGG CACCACCTTC GTTGGAGAGC TCGGTGAGCA      4260

AGCTGCACAC GCCAACAATA TGTATGAGAA TGCTAAACAT ATGAAACCCA TTTACACTGC      4320

AGCCTTAAAA GATGAACTAG TCAAGCCAGA AAAGATTTAT CAAAAAGTCA AGAAGCGTCT      4380

ACTATGGGGC GCCGATCTCG GAACAGTGGT CAGGGCCGCC CGGGCTTTTG GCCCATTTTG      4440

TGACGCTATA AAATCACATG TCATCAAATT GCCAATAAAA GTTGGCATGA ACACAATAGA      4500

AGATGGCCCC CTCATCTATG CTGAGCATGC TAAATATAAG AATCATTTTG ATGCAGATTA      4560

TACAGCATGG GACTCAACAC AAAATAGACA AATTATGACA GAATCCTTCT CCATTATGTC      4620

GCGCCTTACG GCCTCACCAG AATTGGCCGA GGTTGTGGCC CAAGATTTGC TAGCACCATC      4680

TGAGATGGAT GTAGGTGATT ATGTCATCAG GGTCAAAGAG GGGCTGCCAT CTGGATTCCC      4740

ATGTACTTCC CAGGTGAACA GCATAAATCA CTGGATAATT ACTCTCTGTG CACTGTCTGA      4800

GGCCACTGGT TTATCACCTG ATGTGGTGCA ATCCATGTCA TATTTCTCAT TTTATGGTGA      4860

TGATGAGATT GTGTCAACTG ACATAGATTT TGACCCAGCC CGCCTCACTC AAATTCTCAA      4920

GGAATATGGC CTCAAACCAA CAAGGCCTGA CAAAACAGAA GGACCAATAC AAGTGAGGAA      4980

AAATGTGGAT GGACTGGTCT TCTTGCGGCG CACCATTTCC CGTGATGCGG CAGGGTTCCA      5040

AGGCAGGTTA GATAGGGCTT CGATTGAACG CCAAATCTTC TGGACCCGCG GCCCAATCA      5100

TTCAGATCCA TCAGAGACTC TAGTGCCACA CACTCAAAGA AAAATACAGT TGATTTCACT      5160

TCTAGGGGAA GCTTCACTCC ATGGTGAGAA ATTTTACAGA AAGATTTCCA GCAAGGTCAT      5220

ACATGAAATC AAGACTGGTG GATTGGAAAT GTATGTCCCA GGATGGCAGG CCATGTTCCG      5280

CTGGATGCGC TTCCATGACC TCGGATTGTG GACAGGAGAT CGCGATCTTC TGCCCGAATT      5340

CGTAAATGAT GATGCGTCTA AGGACGCTAC ATCAAGCGTG GATGGCGCTA GTGGCGCTGG      5400

TCAGTTGGTA CCGGAGGTTA ATGCTTCTGA CCCTCTTGCA ATGGATCCTG TAGCAGGTTC      5460

TTCGACAGCA GTCGCGACTG CTGGACAAGT TAATCCTATT GATCCCTGGA TAATTAATAA      5520

TTTTGTGCAA GCCCCCCAAG GTGAATTTAC TATTTCCCCA AATAATACCC CCGGTGATGT      5580

TTTGTTTGAT TTGAGTTTGG GTCCCCATCT TAATCCTTTC TTGCTCCATC TATCACAAAT      5640

GTATAATGGT TGGGTTGGTA ACATGAGAGT CAGGATTATG CTAGCTGGTA ATGCCTTTAC      5700

TGCGGGGAAG ATAATAGTTT CCTGCATACC CCCTGGTTTT GGTTCACATA ATCTTACTAT      5760

AGCACAAGCA ACTCTCTTTC CACATGTGAT TGCTGATGTT AGGACTCTAG ACCCCATTGA      5820

GGTGCCTTTG GAAGATGTTA GGAATGTTCT CTTTCATAAT AATGATAGAA ATCAACAAAC      5880

CATGCGCCTT GTGTGCATGC TGTACACCCC CCTCCGCACT GGTGGTGGTA CTGGTGATTC      5940

TTTTGTAGTT GCAGGGCGAG TTATGACTTG CCCCAGTCCT GATTTTAATT TCTTGTTTTT      6000

AGTCCCTCCT ACGGTGGAGC AGAAAACCAG GCCCTTCACA CTCCCAAATC TGCCATTGAG      6060

TTCTCTGTCT AACTCACGTG CCCCTCTCCC AATCAGTAGT ATGGGCATTT CCCCAGACAA      6120

TGTCCAGAGT GTGCAGTTCC AAAATGGTCG GTGTACTCTG GATGGCCGCC TGGTTGGCAC      6180

CACCCCAGTT TCATTGTCAC ATGTTGCCAA GATAAGAGGG ACCTCCAATG GCACTGTAAT      6240
```

-continued

```
CAACCTTACT GAATTGGATG GCACACCCTT TCACCCTTTT GAGGGCCCTG CCCCCATTGG   6300
GTTTCCAGAC CTCGGTGGTT GTGATTGGCA TATCAATATG ACACAGTTTG GCCATTCTAG   6360
CCAGACCCAG TATGATGTAG ACACCACCCC TGACACTTTT GTCCCCCATC TTGGTTCAAT   6420
TCAGGCAAAT GGCATTGGCA GTGGTAATTA TGTTGGTGTT CTTAGCTGGA TTTCCCCCCC   6480
ATCACACCCG TCTGGCTCCC AAGTTGACCT TTGGAAGATC CCCAATTATG GGTCAAGTAT   6540
TACGGAGGCA ACACATCTAG CCCCTTCTGT ATACCCCCCT GGTTTCGGAG AGGTATTGGT   6600
CTTTTTCATG TCAAAAATGC CAGGTCCTGG TGCTTATAAT TTGCCCTGTC TATTACCACA   6660
AGAGTACATT TCACATCTTG CTAGTGAACA AGCCCCTACT GTAGGTGAGG CTGCCCTGCT   6720
CCACTATGTT GACCCTGATA CCGGTCGGAA TCTTGGGGAA TTCAAAGCAT ACCCTGATGG   6780
TTTCCTCACT TGTGTCCCCA ATGGGGCTAG CTCGGGTCCA CAACAGCTGC CGATCAATGG   6840
GGTCTTTGTC TTTGTTTCAT GGGTGTCCAG ATTTTATCAA TTAAAGCCTG TGGGAACTGC   6900
CAGCTCGGCA AGAGGTAGGC TTGGTCTGCG CCGATAATGG CCCAAGCCAT AATTGGTGCA   6960
ATTGCTGCTT CCACAGCAGG TAGTGCTCTG GGAGCGGGCA TACAGGTTGG TGGCGACAGG   7020
CCCTCCAAAG CCAAAGGTAT CAACAAAATT TGCAACTGCA AGAAAATTCT TTTAAACATG   7080
ACAGGGAAAT GATTGGGTAT CAGGTTGAAG CTTCAAATCA ATTATTGGCT AAAAATTTGG   7140
CAACTAGATA TTCACTCCTC CGTGCTGGGG GTTTGACCAG TGCTGATGCA GCAAGATCTG   7200
TGGCAGGAGC TCCAGTCACC CGCATTGTAG ATTGGAATGG CGTGAGAGTG TCTGCTCCCG   7260
AGTCCTCTGC TACCACATTG AGATCCGGTG GCTTCATGTG AGTTCCCATA CCATTTGCCT   7320
CTAAGCAAAA ACAGGTTCAA TCATCTGGTA TTAGTAATCC AAATTATTCC CCTTCATCCA   7380
TTTCTCGAAC CACTAGTTGG GTCGAGTCAC AAAACTCATC GAGATTTGGA AATCTTTCTC   7440
CATACCACGC GGAGGCTCTC AATACAGTGT GGTTGACTCC ACCCGGTTCA ACAGCCTCTT   7500
CTACACTGTC TTCTGTGCCA CGTGGTTATT TCAATACAGA CAGGTTGCCA TTATTCGCAA   7560
ATAATAGGCG ATGATGTTGT AATATGAAAT GTGGGCATCA TATTCATTTA ATTAGGTTTA   7620
ATTAGGTTTA ATTTGATGTT AAAAAAAAAA AAAAAAAAAA AAAAAAAAAA AAAAAAAAAA   7680
AAAAAAAAAA AAAAAAAAAA AAAAAAAAAA AAAAAAAAAA AA                      7722
```

(2) INFORMATION FOR SEQ ID NO:2:

(i) SEQUENCE CHARACTERISTICS:
(A) LENGTH: 381 base pairs
(B) TYPE: nucleic acid
(C) STRANDEDNESS: single
(D) TOPOLOGY: unknown (ii) MOLECULE TYPE: cDNA (vi) ORIGINAL SOURCE:
(A) ORGANISM: Norwalk virus
(B) STRAIN: 8FIIa
(C) INDIVIDUAL ISOLATE: 8FIIa (xi) SEQUENCE DESCRIPTION: SEQ ID NO:2:

```
CATTTTGATG CAGATTATAC AGCATGGGAC TCAACACAAA ATAGACAAAT TATGACAGAA     60
TCCTTCTCCA TTATGTCGCG CCTTACGGCC TCACCAGAAT TGGCCGAGGT TGTGGCCCAA    120
GATTTGCTAG CACCATCTGA GATGGATGTA GGTGATTATG TCATCAGGGT CAAAGAGGGG    180
CTGCCATCTG GATTCCCATG TACTTCCCAG GTGAACAGCA TAAATCACTG GATAATTACT    240
CTCTGTGCAC TGTCTGAGGC CACTGGTTTA TCACCTGATG TGGTGCAATC CATGTCATAT    300
```

```
TTCTCATTTT ATGGTGATGA TGAGATTGTG TCAACTGACA TAGATTTTGA CCCAGCCCGC    360

CTCACTCAAA TTCTCAAGGA A                                              381
```

(2) INFORMATION FOR SEQ ID NO:3:

(i) SEQUENCE CHARACTERISTICS:
        (A) LENGTH: 127 amino acids
        (B) TYPE: amino acid
        (D) TOPOLOGY: linear (ii) MOLECULE TYPE: peptide (vi) ORIGINAL SOURCE:
        (A) ORGANISM:  Norwalk virus (xi) SEQUENCE DESCRIPTION: SEQ ID NO:3:

```
His Phe Asp Ala Asp Tyr Thr Ala Trp Asp Ser Thr Gln Asn Arg Gln
1               5                   10                  15

Ile Met Thr Glu Ser Phe Ser Thr Met Ser Arg Leu Thr Ala Ser Pro
            20                  25                  30

Glu Leu Ala Glu Val Val Ala Gln Asp Leu Leu Ala Pro Ser Glu Met
        35                  40                  45

Asp Val Gly Asp Tyr Val Ile Arg Val Lys Glu Gly Leu Pro Ser Gly
    50                  55                  60

Phe Pro Cys Thr Ser Gln Val Asn Ser Ile Asn His Trp Ile Ile Thr
65                  70                  75                  80

Leu Cys Ala Leu Ser Glu Ala Thr Gly Leu Ser Pro Asp Val Val Gln
                85                  90                  95

Ser Met Ser Tyr Phe Ser Phe Tyr Gly Asp Asp Glu Ile Val Ser Thr
            100                 105                 110

Asp Ile Asp Phe Asp Pro Ala Arg Leu Thr Gln Ile Leu Lys Glu
        115                 120                 125
```

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:4:

```
CACGCGGAGG CTCTCAAT                                                  18
```

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:5:

```
GGTGGCGACA GGCCCTCC                                                  18
```

(2) INFORMATION FOR SEQ ID NO:6:

(i) SEQUENCE CHARACTERISTICS:
        (A) LENGTH: 18 base pairs
        (B) TYPE: nucleic acid -continued

```
            (C) STRANDEDNESS: single
            (D) TOPOLOGY: unknown (ii) MOLECULE TYPE: cDNA (xi) SEQUENCE DESCRIPTION: SEQ ID NO:6:

TCAGCAGTTA TAGATATG                                                    18

(2) INFORMATION FOR SEQ ID NO:7:

(i) SEQUENCE CHARACTERISTICS:
            (A) LENGTH: 18 base pairs
            (B) TYPE: nucleic acid
            (C) STRANDEDNESS: single
            (D) TOPOLOGY: unknown (ii) MOLECULE TYPE: cDNA (xi) SEQUENCE DESCRIPTION: SEQ ID NO:7:

ATGCTATATA CATAGGTC                                                    18

(2) INFORMATION FOR SEQ ID NO:8:

(i) SEQUENCE CHARACTERISTICS:
            (A) LENGTH: 18 base pairs
            (B) TYPE: nucleic acid
            (C) STRANDEDNESS: single
            (D) TOPOLOGY: unknown (ii) MOLECULE TYPE: cDNA (xi) SEQUENCE DESCRIPTION: SEQ ID NO:8:

CAACAGGTAC TACGTGAC                                                    18

(2) INFORMATION FOR SEQ ID NO:9:

(i) SEQUENCE CHARACTERISTICS:
            (A) LENGTH: 18 base pairs
            (B) TYPE: nucleic acid
            (C) STRANDEDNESS: single
            (D) TOPOLOGY: unknown (ii) MOLECULE TYPE: cDNA (xi) SEQUENCE DESCRIPTION: SEQ ID NO:9:

TGTGGCCCAA GATTTGCT                                                    18
```

1. A hybridoma which produces a high affinity monoclonal antibody to a Norwalk virus protein or peptide or to a Norwalk-related virus protein or peptide specifically immunoreactive with a protein or peptide coded for by the coding sequence of a cDNA selected from the group consisting of a cDNA corresponding to SEQ.ID.NO. 1 or a fragment thereof, a cDNA obtained by screening a cDNA library of a Norwalk-related virus with the coding sequence of a cDNA of SEQ ID NO. 1 or a fragment thereof, and a cDNA obtained by screening a cDNA library of a Norwalk-related virus with a cDNA identified by screening a cDNA library of a Norwalk-related virus with a cDNA of SEQ. ID. NO. 1 or a fragment thereof;

whereby said antibody produced specifically recognizes an antigen of a Norwalk virus protein or peptide or a Norwalk-related virus protein or peptide.

2. A high affinity monoclonal antibody produced by the hybridoma of claim 1.

3. A method of producing antibodies to a Norwalk virus protein or peptide or to a Norwalk-related virus protein or peptide comprising:

synthesizing a synthetic protein or peptide of at least 15 amino acids in length and coded for by the coding sequence of a cDNA selected from the group consisting of a cDNA corresponding to SEQ.ID.NO. 1 or a fragment thereof, a cDNA obtained by screening a cDNA library of a Norwalk-related virus with the coding sequence of a cDNA of SEQ ID NO. 1 or a fragment thereof, and a cDNA obtained by screening a cDNA library of a Norwalk-related virus with a cDNA identified by screening a cDNA library of a Norwalk-related virus with a cDNA of SEQ. ID. NO. 1 or a fragment thereof;

immunizing an animal with said synthetic protein or peptide; and recovering antibodies from said animal;

whereby said antibodies specifically recognize an antigen of a Norwalk virus protein or peptide or a Norwalk-related virus protein or peptide.

4. A method of producing a hybridoma which produces a monoclonal antibody to a Norwalk virus protein or peptide or to a Norwalk-related virus protein or peptide comprising the steps of:

synthesizing a protein or peptide of at least 15 amino acids in length and coded for by the coding sequence of a cDNA selected from the group consisting of a cDNA corresponding to SEQ.ID.NO. 1 or a fragment thereof a cDNA obtained by screening a cDNA library of a Norwalk-related virus with the coding sequence of a cDNA of SEQ ID NO. 1 or a fragment thereof, and a cDNA obtained by screening a cDNA library of a Norwalk-related virus with a cDNA identified by screening a cDNA library of a Norwalk-related virus with a cDNA of SEQ. ID. NO. 1 or a fragment thereof;

immunizing an animal with said protein or peptide to produce an antigenic response;

boosting said immunized animal with said protein or peptide to increase polyclonal antibody production in said animal;

fusing splenocytes from said animal with myeloma cells;

screening said fused cells for production of monoclonal antibodies immunoreactive with said protein or peptide; and recovering said monoclonal antibodies;

whereby said monoclonal antibodies specifically recognize an antigen of a Norwalk virus protein or peptide or a Norwalk-related virus protein or peptide.

5. A polyclonal antibody to a Norwalk virus protein or peptide or to a Norwalk-related virus protein or peptide produced according to a process having the following steps:

selecting a cDNA molecule from the group consisting of a cDNA corresponding to the coding sequence of SEQ.ID.NO. 1, or a fragment thereof, a cDNA obtained by screening a cDNA library of a Norwalk-related virus with the coding sequence of a cDNA of SEQ ID NO. 1 or a fragment thereof, and a cDNA obtained by screening a cDNA library of a Norwalk-related virus with a cDNA identified by screening a cDNA library of a Norwalk-related virus with a cDNA of SEQ. ID. NO. 1 or a fragment thereof, wherein said cDNA molecule codes for a protein or peptide of at least 15 amino acids in length;

expressing said cDNA in an expression system to produce a protein or peptide;

immunizing an animal with said protein or peptide;

immunizing said animal with said protein or peptide a second time; and recovering antibodies from said animal;

whereby said antibodies specifically recognize an antigen or a Norwalk virus protein or peptide or a Norwalk-related protein or peptide.

6. A hybridoma which produces a high affinity monoclonal antibody to a Norwalk virus protein or peptide or to a Norwalk-related virus protein or peptide produced according to a process having the following steps:

selecting a cDNA molecule from the group consisting of a cDNA corresponding to the coding sequence of SEQ.ID.NO. 1, or a fragment thereof, a cDNA obtained by screening a cDNA library of a Norwalk-related virus with the coding sequence of a cDNA of SEQ ID NO. 1 or a fragment thereof, and a cDNA obtained by screening a cDNA library of a Norwalk-related virus with a cDNA identified by screening a cDNA library of a Norwalk-related virus with a cDNA of SEQ. ID. NO. 1 or a fragment thereof, wherein said cDNA molecule codes for a protein or peptide of at least 15 amino acids in length;

expressing said cDNA in an expression system to produce a protein or peptide;

immunizing an animal with said protein or peptide;

immunizing said animal with said protein or peptide a second time;

fusing splenocytes of said animal with myeloma cells;

screening said fused cells for production of monoclonal antibodies immunoreactive with said protein or peptide; and recovering said monoclonal antibodies;

whereby said monoclonal antibodies specifically recognize an antigen of a Norwalk virus protein or peptide or a Norwalk-related virus protein or peptide.

7. A high affinity monoclonal antibody to a Norwalk virus protein or peptide or to a Norwalk-related virus protein or peptide produced according to a process having the following steps:

selecting a cDNA molecule from the group consisting of a cDNA corresponding to the coding sequence of SEQ.ID.NO. 1, or a fragment thereof, a cDNA obtained by screening a cDNA library of a Norwalk-related virus with the coding sequence of a cDNA of SEQ ID NO. 1 or a fragment thereof, and a cDNA obtained by screening a cDNA library of a Norwalk-related virus with a cDNA identified by screening a cDNA library of a Norwalk-related virus with a cDNA of SEQ. ID. NO. 1 or a fragment thereof, wherein said cDNA molecules codes for a protein or peptide of at least 15 amino acids in length;

expressing said cDNA in an expression system to produce a protein or peptide;

immunizing an animal with said protein or peptide;

immunizing said animal with said protein or peptide a second time;

fusing splenocytes from said animal with myeloma cells;

screening said cells for the production of monoclonal antibodies immunoreactive with said protein or peptide; and recovering said monoclonal antibodies;

whereby said monoclonal antibodies specifically recognize an antigen of a Norwalk virus protein or peptide or a Norwalk-related virus protein or peptide.

8. A polyclonal antibody to a Norwalk virus protein or peptide or to a Norwalk-related virus protein or peptide produced according to a process having the following steps:

synthesizing a protein or peptide at least 15 amino acids in length and coded for by the coding sequence of a cDNA selected from the group consisting of a cDNA corresponding to SEQ.ID.NO. 1 or a fragment thereof, a cDNA obtained by screening a cDNA library of a Norwalk-related virus with the coding sequence of a cDNA of SEQ ID NO. 1 or a fragment thereof, and a cDNA obtained by screening a cDNA library of a Norwalk-related virus with a cDNA identified by screening a cDNA library of a Norwalk-related virus with a cDNA of SEQ. ID. NO. 1 or a fragment thereof;

immunizing an animal with said protein or peptide;

immunizing said animal with said protein or peptide a second time; and recovering antibodies from said animal;

whereby said antibodies specifically recognize an antigen of a Norwalk virus protein or peptide or a Norwalk-related virus protein or peptide.

9. A hybridoma which produces a high affinity monoclonal antibody to a Norwalk virus protein or peptide or to a Norwalk-related virus protein or peptide produced according to a process having the following steps:

synthesizing a protein or peptide at least 15 amino acids in length and coded for by the coding sequence of a cDNA selected from the group consisting of a cDNA corresponding to SEQ.ID.NO. 1 or a fragment thereof, a cDNA obtained by screening a cDNA library of a Norwalk-related virus with the coding sequence of a cDNA of SEQ ID NO. 1 or a fragment thereof, and a cDNA obtained by screening a cDNA library of a Norwalk-related virus with a cDNA identified by screening a cDNA library of a Norwalk-related virus with a cDNA of SEQ. ID. NO. 1 or a fragment thereof;

immunizing an animal with said protein or peptide;

immunizing said animal with said protein or peptide a second time;

fusing splenocytes of said animal with myeloma cells;

screening said fused cells for production of monoclonal antibodies immunoreactive with said protein or peptide; and recovering said monoclonal antibodies;

whereby said monoclonal antibodies specifically recognize an antigen or a Norwalk virus protein or peptide or a Norwalk-related virus protein or peptide.

10. A high affinity monoclonal antibody to a Norwalk virus protein or peptide or to a Norwalk-related virus protein or peptide produced according to a process having the following steps:

synthesizing a protein or peptide at least 15 amino acids in length and coded for by the coding sequence of a cDNA selected from the group consisting of a cDNA corresponding to SEQ.ID.NO. 1 or a fragment thereof, a cDNA obtained by screening a cDNA library of a Norwalk-related virus with the coding sequence of a cDNA of SEQ ID NO. 1 or a fragment thereof, and a cDNA obtained by screening a cDNA library of a Norwalk-related virus with a cDNA identified by screening a cDNA library of a Norwalk-related virus with a cDNA of SEQ. ID. NO. 1 or a fragment thereof;

immunizing an animal with said protein or peptide;

immunizing said animal with said protein or peptide a second time;

fusing splenocytes from said animal with myeloma cells;

screening said cells for the production of monoclonal antibodies immunoreactive with said protein or peptide; and recovering said monoclonal antibodies;

whereby said monoclonal antibodies specifically recognize an antigen of a Norwalk virus protein or peptide or a Norwalk-related virus protein or peptide.

11. A method of producing antibodies to a Norwalk virus protein or peptide or to a Norwalk-related virus protein or peptide comprising immunizing an animal with a single protein or protein coded for by the coding sequence of a cDNA selected from the group consisting of a cDNA corresponding to SEQ.ID.NO. 1 or a fragment thereof, a cDNA obtained by screening a cDNA library of a Norwalk-related virus with the coding sequence of a cDNA of SEQ ID NO. 1 or a fragment thereof, and a cDNA obtained by screening a cDNA library of a Norwalk-related virus with a cDNA identified by screening a cDNa library of a Norwalk-related virus with a cDNA of SEQ. ID. NO. 1 or a fragment thereof, and recovering antibodies from said animal;

whereby said antibodies specifically recognize an antigen of a Norwalk virus protein or peptide or a Norwalk-related virus protein or peptide.

12. A method of producing a hybridoma which produces a monoclonal antibody to a Norwalk virus protein or peptide or to a Norwalk-related virus protein or peptide comprising the steps of:

immunizing an animal with a protein or peptide coded for by the coding sequence of a cDNA selected from the group consisting of a cDNA corresponding to SEQ ID NO. 1 or a fragment thereof, a cDNA obtained by screening a cDNA library of a Norwalk-related virus with the coding sequence of a cDNA of SEQ ID NO. 1 or a fragment thereof, and a cDNA obtained by screening a cDNA library of a Norwalk-related virus with a cDNA identified by screening a cDNA library of a Norwalk-related virus with a cDNA of SEQ. ID. NO. 1 or a fragment thereof;

boosting said immunization with said protein or peptide to increase antibody production in said animal;

fusing splenocytes from said animal with myeloma cells;

screening said fused cells for production of monoclonal antibodies immunoreactive with said protein or peptide; and recovering said monoclonal antibodies;

whereby said monoclonal antibodies specifically recognize an antigen of a Norwalk virus protein or peptide or a Norwalk-related virus protein or peptide.

13. A method of obtaining monoclonal antibodies to a Norwalk virus protein or peptide or to a Norwalk-related virus protein or peptide comprising:

screening hybridomas with a recombinant or synthetic peptide or protein, said peptide or protein being coded for by the coding sequence of a cDNA selected from the group consisting of a cDNA corresponding to SEQ ID NO. 1 or a fragment thereof, a cDNA obtained by screening a cDNA library of a Norwalk-related virus with the coding sequence of a cDNA of SEQ ID NO. 1 or a fragment thereof, and a cDNA obtained by screening a cDNA library of a Norwalk-related virus with a cDNA identified by screening a cDNA library of a Norwalk-related virus with a cDNA of SEQ. ID. NO. 1 or a fragment thereof; wherein said hybridomas are the fusion product of a myeloma cell and a splenocyte from an animal exposed to a Norwalk virus protein or peptide or a Norwalk related virus protein or peptide and harvesting monoclonal antibodies from the hybridomas which produces antibodies which react with said recombinant or synthetic peptide or protein;

whereby said monoclonal antibodies specifically recognize an antigen of a Norwalk virus protein or peptide or a Norwalk-related virus protein or peptide.

14. A method of obtaining monoclonal antibodies to a Norwalk virus protein or peptide or to a Norwalk-related virus protein or peptide comprising:

harvesting monoclonal antibodies from a hybridoma which produces a monoclonal antibody to a Norwalk virus protein or peptide or to a Norwalk-related virus protein or peptide specifically immunoreactive with a protein or peptide coded for by the coding sequence of a cDNA selected from the group consisting of a cDNA corresponding to SEQ.ID.NO. 1 or a fragment thereof, a cDNA obtained by screening a cDNA library of a Norwalk-related virus with the coding sequence of a cDNA of SEQ ID NO. 1 or a fragment thereof, and a cDNA obtained by screening a cDNA library of a Norwalk-related virus with a cDNA identified by screening a cDNA library of a Norwalk-related virus with a cDNA of SEQ. ID. NO. 1 or a fragment thereof.

* * * * *